United States Patent
Li et al.

(10) Patent No.: US 11,351,157 B2
(45) Date of Patent: Jun. 7, 2022

(54) TREATMENT OF IMMUNOLOGICAL DISEASE USING BERBERINE NANOPARTICLES

(71) Applicants: Icahn School of Medicine at Mount Sinai, New York, NY (US); Sean N. Parker Foundation, San Francisco, CA (US)

(72) Inventors: Xiu-Min Li, New York, NY (US); Changda Liu, New York, NY (US); Kamal Srivatava, New York, NY (US); Haiqiong Yu, New York, NY (US); Sean N Parker, San Francisco, CA (US)

(73) Assignees: Icahn School of Medicine at Mount Sinai, New York, NY (US); Sean N. Parker Foundation, Palo Alto, CA (US)

( * ) Notice: Subject to any disclaimer, the term of this patent is extended or adjusted under 35 U.S.C. 154(b) by 0 days.

(21) Appl. No.: 16/341,582

(22) PCT Filed: Oct. 16, 2017

(86) PCT No.: PCT/US2017/056822
§ 371 (c)(1),
(2) Date: Apr. 12, 2019

(87) PCT Pub. No.: WO2018/071917
PCT Pub. Date: Apr. 19, 2018

(65) Prior Publication Data
US 2020/0276172 A1 Sep. 3, 2020

Related U.S. Application Data

(60) Provisional application No. 62/408,541, filed on Oct. 14, 2016.

(51) Int. Cl.
| | |
|---|---|
| *A61K 31/4375* | (2006.01) |
| *A61P 37/08* | (2006.01) |
| *A61K 9/00* | (2006.01) |
| *A61K 9/51* | (2006.01) |
| *A61K 31/727* | (2006.01) |

(52) U.S. Cl.
CPC ........ *A61K 31/4375* (2013.01); *A61K 9/0053* (2013.01); *A61K 9/5161* (2013.01); *A61K 31/727* (2013.01); *A61P 37/08* (2018.01)

(58) Field of Classification Search
None
See application file for complete search history.

(56) References Cited

U.S. PATENT DOCUMENTS

| | | |
|---|---|---|
| 2008/0254078 A1 | 10/2008 | Kauper et al. |
| 2015/0132399 A1 | 5/2015 | Mousa |
| 2016/0175291 A1 | 6/2016 | Xiu-Min et al. |

FOREIGN PATENT DOCUMENTS

| | | |
|---|---|---|
| JP | 2009-511549 | 3/2009 |
| WO | WO 2014/179528 | 11/2014 |

OTHER PUBLICATIONS

Nan Yang PhD et al., Berberine and limonin suppress IgE production by human B cells and peripheral blood mononuclear cells from food-allergic patients, Nov. 2014, Annals of Allergy, Asthma & Immunology, vol. 113, Issue 5. pp. 556-564. (Year: 2014) (Year: 2014).*
Avadi et al., "Ex vivo evaluation of insulin nanoparticles using chitosan and arabic gum," ISRN Pharm, 2011, 860109, 6 pages.
Avadi et al., "Preparation and characterization of insulin nanoparticles using chitosan and Arabic gum with ionic gelation method," Nanomedicine, 2010, 6(1):58-63.
Bowman et al., "Differential biological and adjuvant activities of cholera toxin and *Escherichia coli* heat-labile enterotoxin hybrids," Infect Immun, 2001, 69(3):1528-35.
Chen et al., "Recent advances in chitosan-based nanoparticles for oral delivery of macromolecules," Adv Drug Deliv Rev, 2013, 65(6):865-79.
Erazo et al., "Unique maturation program of the IgE response in vivo," Immunity, 2007, 26(2):191-203.
Gauvreau et al., "Targeting membrane-expressed IgE B cell receptor with an antibody to the MI prime epitope reduces IgE production," Sci Transl Med, 2014, 6(243):243ra85.
Godugu et al., "Approaches to improve the oral bioavailability and effects of novel anticancer drugs berberine and betulinic acid," PLoS One, 2014, 9(3):e89919.
Gui et al., "Preparation and evaluation of a microemulsion for oral delivery of berberine," Pharmazie, 2008, 63:516-519.
Guo et al., "CYP2D plays a major role in berberine metabolism in liver of mice and humans," Xenobiotica, 2011, 41(11):996-1005.
Harris et al., "A randomized trial of quilizumab in adults with refractory chronic spontaneous urticaria," J Allergy Clin Immunol. 2016, 138(6):1730-1732.
Harris et al., "A randomized trial of the efficacy and safety of quilizumab in adults with inadequately controlled allergic asthma," Respir Res, 2016, 17(1):29.
He et al., "Biology of IgE production: IgE cell differentiation and the memory of IgE responses," Curr Top Microbiol Immunol. 2015, 388:1-19.
He et al., "The distinctive germinal center phase ofigE+ B lymphocytes limits their contribution to the classical memory response," J Exp Med, 2013, 210(12):2755-71.
Hendeles et al., "Anti-immunoglobulin E therapy with omalizumab for asthma," Ann Pharmacother, 2007, 41(9):1397-1410.
Jackson et al., "Factors regulating immunoglobulin production by normal and disease-associated plasma cells," Biomolecules, 2015, 5(1):20-40.
Jang et al., "Foxp3+ regulatory T cells control humoral autoimmunity by suppressing the development of long-lived plasma cells," J Immunol, 2011, 186(3):1546-1553.
Lee et al., "Oral administration ofIL-12 suppresses anaphylactic reactions in a murine model of peanut hypersensitivity," Clin Immunol, 2001, 101(2):226-228.

(Continued)

*Primary Examiner* — Nannette Holloman
(74) *Attorney, Agent, or Firm* — Fish & Richardson P.C.

(57) ABSTRACT

The disclosure provides methods of treating immunological conditions, e.g., allergy, by administration of berberine nanoparticles.

10 Claims, 17 Drawing Sheets

(56) References Cited

OTHER PUBLICATIONS

Liu et al., "Combined inhaled diesel exhaust particles and allergen exposure alter methylation of T helper genes and IgE production in vivo," Toxicol Sci., 2008, 102(1):76-81.
Liu et al., "The ligase PIAS 1 restricts natural regulatory T cell differentiation by epigenetic repression," Science, 2010, 330(6003):521-525.
Luger et al. "Allergy for a lifetime?" Allergol Int, 2010, 59(1):1-8.
Meiler et al., "Distinct regulation of IgE, IgG4 and IgA by T regulatory cells and toll-like receptors," Allergy, 2008, 63(11):1455-1463.
Mousavi et al., "Anti-Inflammatory Effects of Heparin and Its Derivatives: A Systematic Review," Adv Pharmacol Sci, 2015, 2015(507151):1-14.
Singh et al., "Berberine and its derivatives: a patent review—(2009-2012)," Expert Opin Ther Pat. 2013, 23(2):215-31.
Song et al., "Maternal allergy increases susceptibility to offspring allergy in association with TH2-biased epigenetic alterations in a mouse model of peanut allergy," J Allergy Clin Immunol, 2014, 134(6):1339-1345.e7
Srivastava et al., "Anti-Asthma Simplified Herbal Medicine Intervention-induced long-lasting tolerance to allergen exposure in an asthma model is interferon-gamma, but not transforining growth factor-beta dependent." ClinExp Allergy, 2010, 40(11):1678-1688.
Srivastava et al., "Efficacy, safety and immunological actions of butanol-extracted Food Allergy Herbal Formula-2 on peanut anaphylaxis," Clin Exp Allergy, 2010, 2011(41):582-591.
Srivastava et al., "The Chinese herbal medicine formula F AHF-2 completely blocks anaphylactic reactions in a murine model of peanut allergy," J Allergy Clin Immunol, 2005, 115(1):171-178.
Wei et al., "Intestinal absorption ofberberine and 8-hydroxy dihydroberberine and their effects on sugar absorption in rat small intestine," J Huazhong Univ Sci Technolog Med Sci, 2014, 34:186-189.
Wu et al., "Targeting IgE production in mice and humans," Curr Opin Immunol, 2014, 31:8-15.
Yang et al.. "Berberine and limonin suppress IgE production by human B cells and peripheral blood mononuclear cells from food-allergic patients," Ann Allergy Asthma Immunol, 2014,113(5):556-64.e4.

Zhang et al., "Intestinal absorption mechanisms of berberine, palmatine. jateorhizine, and coptisine: involvement of P-glycoprotein," Xenobiotica, 2011,41(4):290-296.
EP Search Report in European Appln. No. 17859782.9, dated May 26, 2020, 10 pages.
ISA/US, International Search Report for PCT/US2017/056822 (dated Dec. 22, 2017).
(Chang, C-H et al.) Development of novel nanoparticles shelled with heparin for berberine 1-2, 3/1-2, 6/3/1-2, delivery to treat Helicobacter pylori. Acta Biomaterialia, vol. 7, No. 2, pp. 593-603. Feb. 28 7/6/3/1-2 2011; title; abstract; pp. 593-594, 596-597.
(Wu, S-J et al.) Delivery of Berberine Using Chitosan/Fucoidan-Taurine Conjugate 1-2, 3/1-2, 6/3/1-2, Nanoparticles for Treatment of Defective Intestinal Epithelial Tight Junction Barrier. Marine 7/6/3/1-2 Drugs, vol. 12, pp. 5677-5697. Nov. 24, 2014; entire document.
(Khemani, M et al.) Encapsulation of Berberine in Nano-Sized PLGA Synthesized by 1-2, 3/1-2, 6/3/1-2, Emulsification Method. International Scholarly Research Network Nanotechnology, 177/6/3/1-2 Sep. 2012; entire document.
(Lin, Y-H et al.) Berberine-loaded targeted nanoparticles as specific Helicobacter pylori 1-2, 3/1-2. 6/3/1-2, eradication therapy: in vitro and in vivo study. Nanomedicine, vol. 10, No. 1. Jan. 2015, 7/6/3/1-2 Published Online: Sep. 1, 2014, https://doi.org/10.2217/nnm.14.76; abstract.
CN Office Action in Chinese International Appln. No. 201780077346.3, dated Mar. 23, 2021, 17 pages (with English Translation).
Li., "Helicobacter Pylori and Gastrointestinal Immunity," Gastric Mucosal Injury and Protection: Foundation and Clinical, Apr. 30, 2014, pp. 327-328 (with Machine Translation).
JP Office Action in Japanese Appln. No. 2019-541688, dated Aug. 17, 2021, 16 pages (with English Translation).
International Preliminary Report on Patentability in International Application No. PCT/US2017/056822, dated Apr. 16, 2019, 6 pages.
International Search Report and Written Opinion in International Application No. PCT/US2017/056822, dated Dec. 22, 2017, 8 pages.
Nguyen et al., "Chitosan-coated nano-liposomes for the oral delivery of berberine hydrochloride," Journal of Materials Chemistry B, 2014, 2, 7149-7159.

* cited by examiner

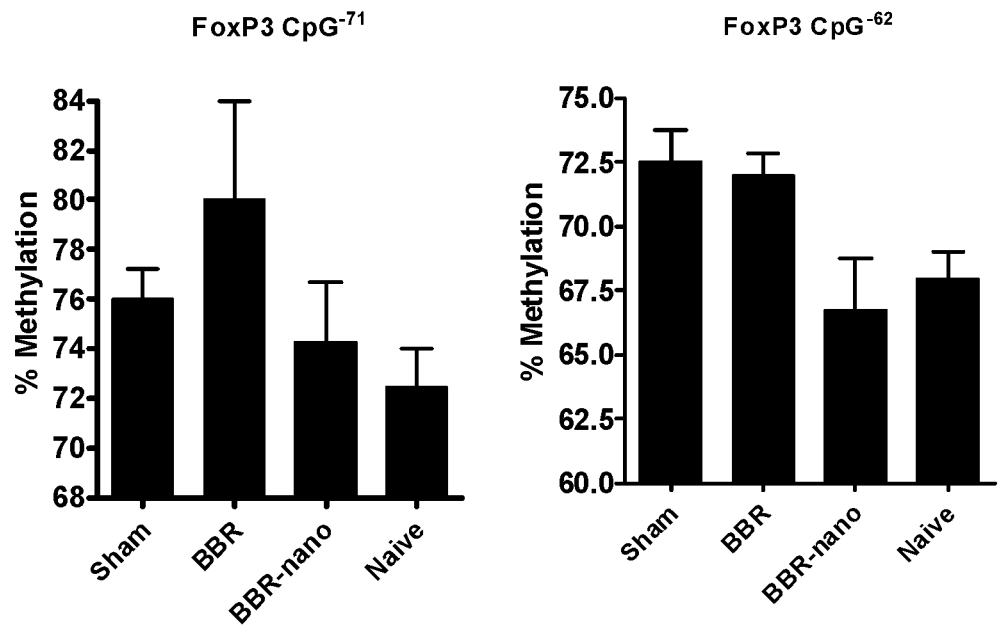
FIGURE 9A
FIGURE 9B
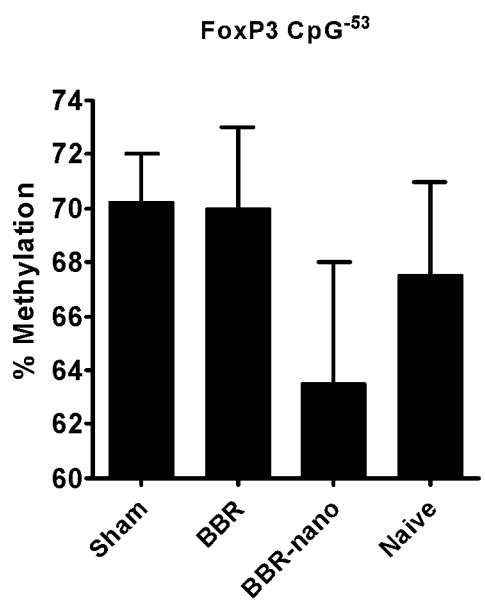
FIGURE 9C

TREATMENT OF IMMUNOLOGICAL DISEASE USING BERBERINE NANOPARTICLES

CROSS-REFERENCE TO RELATED APPLICATIONS

This application claims the benefit of U.S. Provisional Application No. 62/408,541, filed Oct. 14, 2016, which is incorporated herein by reference in its entirety.

GOVERNMENT SUPPORT

This invention was made with government support under AT002647 and AT001495 awarded by the National Institutes of Health. The government has certain rights in the invention.

TECHNICAL FIELD

This disclosure relates to treatment of immunological conditions such as allergy, and more particularly to treatment of immunological conditions such as allergy.

BACKGROUND

IgE-mediated anaphylactic reactions often have serious and sometimes fatal health consequences for those suffering from food allergy. Therapies that can dramatically reduce IgE have been elusive.

IgE plays a central role in the pathology of allergic diseases such as food allergy, allergic asthma, allergic rhinitis, and many others. Persistent allergic conditions such as lifelong food allergy and allergic asthma imply chronic presence of allergen-specific IgE and specific therapies to reduce IgE are extremely limited. Standard treatments for asthma and other allergic conditions are sub-optimally effective for many patients, and there is no FDA approved medicine for IgE mediated food allergy.

Research into the development of non-steroid treatments of allergic conditions is of importance given the adverse side effects of chronic steroids. Anti-IgE antibody administration, which provides an additional option for treating allergic conditions by targeting IgE molecules, has been incorporated into the treatment of poorly controlled asthma. However, continuing monthly injections are needed to maintain effect because although this treatment neutralizes secreted IgE, it does not stop B cell IgE production. There is ongoing research into use of mIgE (membrane-bound IgE) targeting antibodies that purportedly deplete IgE-B cells however early human studies with quilizumab, the first of this type of biologic to studied in clinical trials, has shown only moderate IgE reduction without any significant clinical benefit. Hendeles et al., Anti-immunoglobulin E therapy with omalizumab for asthma. *Ann. Pharmacother.*, 2007, 41, 1397-410; Luger et al., Allergy for a lifetime? *Allergol. Int.*, 2010, 59, 1-8; Gauvreau, et al., Targeting membrane-expressed IgE B cell receptor with an antibody to the M1 prime epitope reduces IgE production. *Sci. Transl. Med.*, 2014, 6, 243ra85; Harris et al., A randomized trial of quilizumab in adults with refractory chronic spontaneous urticaria. *J. Allergy Clin. Immunol.*, 2016, 138(6), 1730-1732; Harris et al., A randomized trial of the efficacy and safety of quilizumab in adults with inadequately controlled allergic asthma. *Respir. Res.*, 2016, 17, 29.

A method of inhibiting IgE production by B cells, particularly the memory IgE response, would be an important novel anti-IgE therapy. In the past few years it was showed that the traditional Chinese medicine (TCM) formulas FAHF-2 and ASHMI are effective alternative therapies for food allergy and asthma that provide comprehensive anti-allergic immune benefits, including reduction of antigen-specific IgE and allergic inflammation. Srivastava et al. The Chinese herbal medicine formula FAHF-2 completely blocks anaphylactic reactions in a murine model of peanut allergy. *J. Allergy Clin. Immunol.* 2005, 115, 171-8; Srivastava et al., Anti-Asthma Simplified Herbal Medicine Intervention-induced long-lasting tolerance to allergen exposure in an asthma model is interferon-gamma, but not transforming growth factor-beta dependent. *Clin. Exp. Allergy* 2010, 40, 1678-88. However, continued research is needed to increase the ease and potency of products.

Berberine (BBR), an isoquinoline alkaloid compound isolated from Phellodendron amurens, an herbal constituent of FAHF-2, and butanol refined FAHF-2 (B-FAHF-2), significantly reduced IgE production by human B cells and peripheral blood mononuclear cells (PBMCs) from patients with food allergy. Yang et al., Berberine and limonin suppress IgE production by human B cells and peripheral blood mononuclear cells from food-allergic patients. *Ann. Allergy Asthma Immunol.*, 2014, 113, 556-64.e4. Its $IC_{50}$ value is as low as 0.1962 μg/mL. Inhibition in PBMCs is in a non-cytotoxic manner, which is associated with suppression of epsilon germline transcript (EGLT) expression, a key mechanism that promotes IgE isotype switching. Yang et al., Berberine and limonin suppress IgE production by human B cells and peripheral blood mononuclear cells from food-allergic patients. Ann. Allergy Asthma Immunol., 2014, 113, 556-64.e4. This finding suggested that berberine might have the potential to be developed as an anti-IgE therapy.

Although berberine is one of the most frequently used herbal medications in East Asia, and has various pharmacological activities including anti-inflammatory actions, its clinical application is limited by its poor bioavailability. Singh et al., Berberine and its derivatives: a patent review (2009-2012). *Expert. Opin. Ther. Pat.*, 2013, 23, 215-31. Berberine bioavailability is usually less than 1%. Godugu et al., Approaches to improve the oral bioavailability and effects of novel anticancer drugs berberine and betulinic acid. *PLoS One*, 2014, 9, e89919. This is due to the fact that berberine has poor solubility and absorption in the intestine, and it has a high rate of efflux (up to 95%) from intestinal epithelial cells mediated by P-glycoprotein. Wei et al., Intestinal absorption of berberine and 8-hydroxy dihydroberberine and their effects on sugar absorption in rat small intestine. *J. Huazhong Univ. Sci. Technolog. Med. Sci.*, 2014, 34, 186-9; Zhang et al. Intestinal absorption mechanisms of berberine, palmatine, jateorhizine, and coptisine: involvement of P-glycoprotein. *Xenobiotica*, 2011, 41, 290-6. It is also largely metabolized during the first pass through the liver. Guo et al., CYP2D plays a major role in berberine metabolism in liver of mice and humans. *Xenobiotica*, 2011, 41, 996-1005. It was found that the maximal berberine level obtained with the dose ($C_{max}$) and area under the curve (AUC) of berberine when given as a component of B-FAHF-2 was many fold higher than the $C_{max}$ and AUC of double the amount of berberine in B-FAHF-2 given alone. Thus, some components in B-FAHF-2 increase bioavailability and/or decrease clearance of berberine.

Nano-medicine techniques have been studied as potential improved delivery methods to increase berberine bioavailability. Godugu et al., Approaches to improve the oral bioavailability and effects of novel anticancer drugs berberine and betulinic acid. *PLoS One*, 2014, 9, e89919; Gui et al., Preparation and evaluation of a microemulsion for oral delivery of berberine. *Pharmazie,* 2008, 63, 516-9.

It has therefore been found that berberine is capable of directly inhibiting IgE production in cell culture but medical application of berberine for IgE is problematic due to poor bioavailability.

SUMMARY

The present disclosure describes that oral administration of nanoparticulate berberine, e.g., berberine encapsulated in heparin/chitosan nanoparticles results in substantial and sustained reduction of IgE responses, e.g., in a murine model of peanut allergy. The concept was tested by determining the in vivo IgE-reduction ability of berberine delivered within heparin/chitosan nanoparticles.

In brief, berberine/heparin/chitosan nanoparticles (BBR-nano) were prepared by simple ionic gelation. This method yielded nanoparticles with average diameter of 326 μm and zeta potential of approximately −19.79 mV. Mice given one oral dose of berberine/heparin/chitosan nanoparticles had significantly higher levels of berberine in blood compared to mice given berberine alone. For in vivo testing, mice were systemically sensitized to peanut using alum as an adjuvant and subsequently treated with two oral courses of berberine/heparin/chitosan nanoparticles, berberine alone or heparin/chitosan nanoparticles. It was found that treatment with berberine/heparin/chitosan nanoparticles, but not berberine alone, resulted in profound and sustained reduction in peanut-specific IgE. IgE-reduction could be observed after 1 week of therapy and persisted for at least 20 weeks after stopping therapy. Reduction was also observed for total IgE but not for total IgA and peanut-specific IgG1/IgG2a. Additionally, mice treated with berberine/heparin/chitosan nanoparticles were completely protected from anaphylactic symptoms to post-therapy oral peanut challenge and did not show anaphylaxis-associated hypothermia. Finally, mice treated with berberine/heparin/chitosan nanoparticles showed lower IL-4 and high IFN-γ production in restimulated splenocytes and increased percentages of IFN-γ producing CD T cells. Also observed was a significantly lower cumulative methylation of CpG residues in the murine FoxP3 promoter indicating promotion of an anti-allergic and regulatory immune milieu. Therapy with nanoparticulate berberine, and in particular berberine/heparin/chitosan nanoparticles represents a novel treatment for IgE-mediated food allergy with the potential to approach a cure for this disorder because of its ability to abolish IgE responses long-term.

The present disclosure therefore provides a method of treating an immunological disease in a subject in need thereof, comprising an administering to the subject an effective amount of a composition comprising nanoparticles comprising berberine or an analog or derivative of berberine, or a salt thereof, encapsulated in the nanoparticles. In some embodiments, berberine, or a salt thereof, is encapsulated in the nanoparticles.

In some embodiments, the nanoparticles comprise an anionic polymer.

In some embodiments, the anionic polymer is an anionic polysaccharide.

In some embodiments, the anionic polymer is a sulfated polysaccharide.

In some embodiments, the anionic polymer is an anionic aminoglycan polymer.

In some embodiments, the anionic polymer is a sulfated aminoglycan polymer.

In some embodiments, the nanoparticles comprise the berberine, or analog or derivative of berberine, or the salt thereof, and the anionic polymer in a ratio in the range from about 1:5 to about 5:5, e.g., about 1:5; about 2:5; about 3:5; about 4:5 or about 5:5 by weight.

In some embodiments, the nanoparticles comprise heparin.

In some embodiments, the nanoparticles comprise the berberine, or analog or derivative of berberine, or the salt thereof, and heparin in a ratio in the range from about 1:5 to about 5:5, e.g., about 1:5; about 2:5; about 3:5; about 4:5 or about 5:5 by weight.

In some embodiments, the nanoparticles comprise a polysaccharide.

In some embodiments, the nanoparticles comprise a lipopolysaccharide.

In some embodiments, the nanoparticles comprise an aminoglycoside polymer.

In some embodiments, the nanoparticles comprise chitosan.

In some embodiments, the nanoparticles comprise berberine, heparin and chitosan.

In some embodiments, the nanoparticles comprise heparin and chitosan in a ratio of about 5:1 to 5:5 by weight, e.g., about 5:1 to about 5:2.5, e.g., about 5:1, about 5:1.5, about 5:2 or about 5:2.5.

In some embodiments, the nanoparticles comprise berberine, heparin and chitosan in a ratio of about 2:5:1.5, about 3:5:1.5 or about 4:5:1.5 by weight.

In some embodiments, the nanoparticles have a zeta potential in the range from about −10 to about −50 mV, e.g., about −10 mV, about −15 mV, about −20 mV, about −25 mV, about −30 mV, about −35 mV, about −40 mV, about −45 mV, or about −50 mV. In some embodiments, the nanoparticles have a mean particle size in the range from about 5 nm to about 1000 nm, e.g., about 10 nm to about 1000 nm, about 20 nm to about 1000 nm, about 50 nm to about 1000 nm, about 100 nm to about 1000 nm, about 200 nm to about 1000 nm; e.g., about 100 nm, about 200 nm, about 300 nm, about 400 nm, about 500 nm, about 600 nm, about 700 nm, about 800 nm, about 900 nm, or about 1000 nm.

In some embodiments, the composition is administered orally. The composition can also be administered, e.g., by injection or by inhalation.

In some embodiments, the composition is administered repeatedly.

In some embodiments, the composition is administered at a frequency of about once per day.

In some embodiments, the composition is administered at a frequency of about every other day.

In some embodiments, the composition is administered at a frequency of about twice per week.

In some embodiments, the composition is administered at a frequency of about once per week.

In some embodiments, the composition is administered at a frequency of about once per two weeks.

In some embodiments, the composition is administered at a frequency of about twice per month.

In some embodiments, the composition is administered at a frequency of about once per month.

In some embodiments, the composition is administered at a frequency of about once per two months.

In some embodiments, the composition is administered at a frequency of about once per three months.

In some embodiments, the composition is administered at a frequency of about once per four months.

In some embodiments, the composition is administered at a frequency of about once per five months.

In some embodiments, the composition is administered at a frequency of about once per six months.

In some embodiments, the composition is administered at a frequency of about twice per year (semi-annually).

In some embodiments, the composition is administered at a frequency of about once per year (annually).

In some embodiments, the composition is administered at a frequency of about once per two years (biannually).

In some embodiments, a single administration is effective to treat the immunological disease for a period of at least about one week, at least about one month, at least about six months, at least about one year, or at least about two years.

In some embodiments, the immunological disease is an IgE-mediated immunological disease.

In some embodiments, the immunological disease is a B-cell-mediated immunological disease.

In some embodiments, the immunological disorder is selected from allergy, asthma, allergic rhinitis, rheumatoid arthritis, chronic obstructive pulmonary disease, inflammatory bowel disease, Crohn's disease, ulcerative colitis, coeliac disease, psoriasis, type-1 diabetes, systemic lupus erythematosus, Guillain-Barré syndrome, atopic dermatitis, graft-versus-host disease and transplant rejection.

In some embodiments, the immunological disease is allergy.

In some embodiments, the immunological disease is food allergy.

In some embodiments, the immunological disease is food allergy to peanuts, tree nuts (e.g., almond, brazil nuts, cashew nuts, macadamia nuts, or walnuts), soy products, milk products, egg products, fish products, crustacean products, gluten or wheat products.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A plots symptom scores recorded 30 minutes after challenge at 2, 9, 14 and 20 weeks following therapy. The challenges at 2 and 14 weeks were systemic and those at 9 and 20 weeks were oral. Symptom score were assigned using the scoring key 0—no signs; 1—scratching and rubbing around the snout and head, diarrhea without other systemic symptoms; 2—puffiness around the eyes and snout, redness around snout, pilar erecti, reduced activity, and/or decreased activity with increased respiratory rate; 3—Labored respiration, diarrhea accompanied by drop in body temperature, and labored respiration accompanied by drop in body temperature and sustained lack of voluntary motility, but activity after prodding, 4—Labored respiration, drop in body temperature, cyanosis around the mouth and the tail splaying of limbs with belly resting on cage floor, minimal or no activity after prodding, tremor and convulsions. 5—Death. Bars are group medians. FIG. 3B plots body temperatures recorded using a rectal probe immediately after assignment of symptom scores. Boxplots show group means and range. FIG. 3C plots plasma histamine levels in blood samples drawn after symptom scores were recorded measured by ELISA. Bars are group means. N=8-10 mice/group. *$P<0.05$; ***$P<0.001$.

FIG. 6A: IL-4, FIG. 6B: IFNγ and FIG. 6C-IFN-γ/IL-4 ratio. Data shown as group Means±SEM. $P<0.01$; *$P<0.001$ vs Sham (N=4-5 mice/group).

FIG. 7A is a depiction of representative data of flow cytometric analysis showing the percentage of IFN-γ producing CD8 T cells.

FIG. 9A-E are plots of post-therapy methylation percentages of CpG residues in the murine FoxP3 promoter. FIGS. 9A-D are plots that show FoxP3 promoter CpGs assessed by pyrosequencing of bisulfite converted genomic DNA obtained from blood. FIG. 9E is a plot showing Cumulative methylation for all FoxP3 promoter CpGs for each experimental group. Bars indicate group Mean±SEM. N=4-5 mice per group. *$P<0.05$ vs Sham.

DETAILED DESCRIPTION

Definitions

Figure 1:
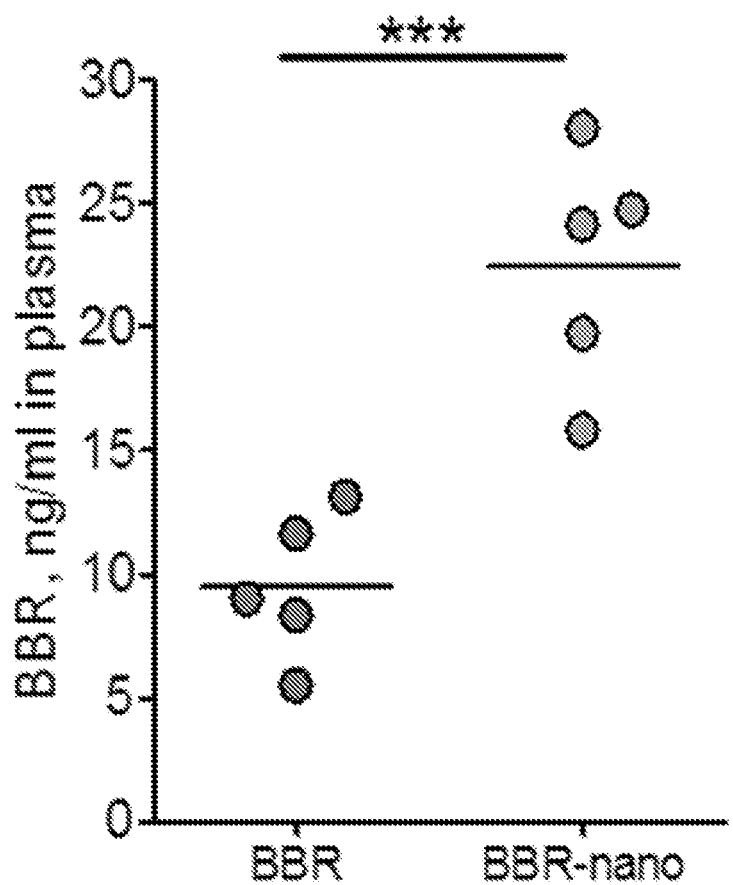
FIG. 1 is a plot of plasma berberine levels after oral administration of berberine alone (BBR) or berberine/heparin/chitosan nanoparticles (BBR-nano). Mice were fasted overnight. One hour following oral administration, blood was collected and BBR levels in plasma were measured by HPLC. Bars indicate group means. N=5 mice per group. ***$P<0.001$ vs BBR.

Unless defined otherwise, all technical and scientific terms used herein have the same meaning as is commonly understood by one of ordinary skill in the art to which this disclosure belongs.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

Berberine is a quaternary ammonium salt from the protoberberine group of benzylisoquinoline alkaloids and has the chemical structure:

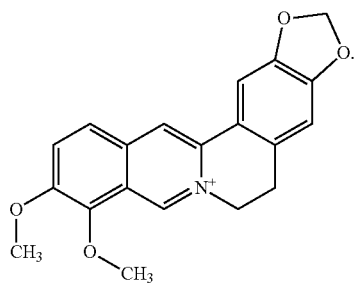 [SMILES: COc1ccc2cc3[n+](cc2c1OC)CCc1cc2c(cc1-3)OCO2]

Berberine can be employed as a salt with a pharmaceutically acceptable anion. The present invention can also be carried out by using berberine analogues in place of berberine. Analogues of berberine include substituted derivatives or homologues of berberine, or other protoberberine or benzylisoquinoline alkaloids.

The term "nanoparticle" as used herein refers to a particle having a size from about 1 nm to about 1000 nm. The term "nanoparticle" can also refer to "microparticles" which have a size in the range from about 1000 nm to about 1 mm.

The term "nanoparticle size" as used herein refers to the median size in a distribution of nanoparticles. The median size is determined from the average linear dimension of individual nanoparticles, e.g., the diameter of a spherical nanoparticle. Size may be determined by any number of methods in the art, including dynamic light scattering (DLS) and transmission electron microscopy (TEM) techniques. In some embodiments, the nanoparticle has a size from about 5 to about 1000 nm, 200 to about 500 nm, and/or from about 200 to about 400 nm.

The term "salt" includes any ionic form of a polymer and one or more counterionic species (cations and/or anions). Salts also include zwitterionic polymers (i.e., a molecule containing one more cationic and anionic species, e.g., zwitterionic amino acids). Counter ions present in a salt can include any cationic, anionic, or zwitterionic species. Exemplary anions include, but are not limited to, chloride, bromide, iodide, nitrate, sulfate, bisulfate, sulfite, bisulfite, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluoromethansulfonate, ethanesulfonate, benzenesulfonate, p-toluenesulfonate, p-trifluoromethylbenzenesulfonate, hydroxide, aluminates and borates. Exemplary cations include, but are not limited to, monovalent alkali metal cations, such as lithium, sodium, potassium and cesium, and divalent alkaline earth metals, such as beryllium, magnesium, calcium, strontium and barium. Also included are transition metal cations, such as gold, silver, copper and zinc, as well as nonmetal cations, such as ammonium salts. Representative organic amines useful for the formation of base addition salts include ethylamine, diethylamine, ethylenediamine, ethanolamine, diethanolamine, piperazine, and the like.

References to a polymer described and disclosed herein are considered to include the free acid, the free base, and all addition salts and complexes of the polymer. The polymers may also form inner salts or zwitterions when a free carboxy and a basic amino group are present concurrently. The term "pharmaceutically acceptable salt" refers to salts which possess toxicity profiles within a range that affords utility in pharmaceutical applications. Preparation and selection of suitable salt forms is described in Stahl et al., *Handbook of Pharmaceutical Salts: Properties, Selection, and Use*, Wiley-VCH 2002.

The phrase "pharmaceutically acceptable" is employed herein to refer to those polymers, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Abbreviations

The following abbreviations may be used herein: AcOH (acetic acid); aq. (aqueous); atm. (atmosphere(s)); Da (dalton(s)); DMF (N,N-dimethylformamide); DMSO (dimethylsulfoxide); Et (ethyl); Et$_3$N or TEA (triethylamine); EtOAc (ethyl acetate); EtOH (ethanol); FBS (fetal bovine serum); h (hour(s)); HPLC (high performance liquid chromatography); M (molar); Me (methyl); MeCN (acetonitrile); MeOH (methanol); mg (milligram(s)); min. (minute(s)); mL (milliliter(s)); mmol (millimole(s)); mV (millivolt(s)); MRI (magnetic resonance imaging); $M_n$ or MW (molecular weight); N (normal); nm (nanometer); nM (nanomolar); NP (nanoparticle); NPs (nanoparticles); nPn (n-pentyl); nPr (n-propyl); PBS (phosphate-buffered saline); rpm (revolutions per minute); s (second(s)); t-Bu (tert-butyl); TTFA (trifluoroacetic acid); THF (tetrahydrofuran); μg (microgram(s)); μL (microliter(s)); μm (micromolar); wt (weight); wt % (weight percent).

Methods of Treatment

In the studies described herein, it has surprisingly been found that nanoparticulate formulations of berberine, or analogs or derivatives of berberine, or salts of berberine, its analogs or derivatives, are surprisingly effective for treating immunological diseases such as allergy, e.g., food allergy. In particular, it has surprisingly been found that treating immunological diseases such as allergy, e.g., food allergy, with nanoparticulate formulations of berberine can provide long-lasting therapeutic and protective effects.

The present disclosure therefore provides a method of treating an immunological disease in a subject in need thereof, comprising an administering to the subject an effective amount of a composition comprising nanoparticles that comprise berberine or analogs or derivatives of berberine, or salts of berberine, its analogs or derivatives.

In some embodiments, the immunological disorder is selected from allergy, asthma, allergic rhinitis, rheumatoid arthritis, chronic obstructive pulmonary disease, inflammatory bowel disease, Crohn's disease, ulcerative colitis, coeliac disease, psoriasis, type-1 diabetes, systemic lupus erythematosus, Guillain-Barré syndrome, atopic dermatitis, graft-versus-host disease and transplant rejection.

In some embodiments, the immunological disease is an IgE-mediated immunological disease, e.g., allergy.

In some embodiments, the immunological disease is a B-cell-mediated immunological disease.

In some embodiments, the immunological disease is allergy. In some embodiments, provided composition comprising nanoparticles that comprise or analogs or derivatives of berberine, or salts of berberine, its analogs or derivatives can be administered to prevent and/or delay the onset of an allergic reaction. In general, nanoparticle compositions as described herein may be used for treatment and/or prevention of any type of allergy. In some embodiments, provided nanoparticle compositions may be used for treatment and/or prevention of an allergy associated with one or more protein allergens. In some embodiments, the nanoparticle compositions may be used for treatment of allergies such as those to pollen allergens, mite allergens, allergens in animal danders (e.g., dog, cat) or excretions (e.g., saliva, urine), and fungi allergens. In some embodiments, the nanoparticle compositions may be used for treatment of allergies associated with anaphylactic allergens, such as food allergens, including, but not limited to, nut allergens (e.g., from peanut, walnut, almond, pecan, cashew, hazelnut, pistachio, pine nut, brazil nut), dairy allergens (e.g., from egg, milk), seed allergens (e.g., from sesame, poppy, mustard), soybean, wheat, and fish allergens (e.g., from shrimp, crab, lobster, clams, mussels, oysters, scallops, crayfish); insect allergens, including but not limited to, bee stings, wasp stings), and rubber allergens (e.g., from latex).

In some embodiments, the immunological disease is food allergy. In some embodiments, the immunological disease is food allergy to peanuts, tree nuts (e.g., almond, brazil nuts, cashew nuts, macadamia nuts, or walnuts), soy products, milk products, egg products, fish products, crustacean products, gluten or wheat products.

Food allergies are mediated through the interaction of IgE to specific proteins contained within the food. Examples of common food allergens include proteins from nuts (e.g., from peanut, walnut, almond, pecan, cashew, hazelnut, pistachio, pine nut, brazil nut), dairy products (e.g., from egg, milk), seeds (e.g., from sesame, poppy, mustard), soybean, wheat, and fish (e.g., shrimp, crab, lobster, clams, mussels, oysters, scallops, crayfish). Examples of common insect allergens include, but are not limited to, proteins from insects such as fleas, ticks, ants, cockroaches, and bees.

The nanoparticulate formulations of berberine, or analogs or derivatives of berberine, or salts of berberine, its analogs or derivatives can be used in a method of treatment to reduce the level of IgE specific to the allergy/allergen to be treated by administering to a subject in need of the treatment an effective amount of a composition comprising nanoparticles that comprise berberine or analogs or derivatives of berberine, or salts of berberine, its analogs or derivatives.

Berberine Nanoparticles

The berberine nanoparticles useful in the methods described herein may include berberine or analogs or derivatives of berberine, or salts of berberine, its analogs or derivatives encapsulated therein.

Analogues of berberine include substituted derivatives or homologues of berberine, or other protoberberine or benzylisoquinoline alkaloids, e.g. as disclosed in Grycova et al., Quaternary Protoberberine Alkaloids, *Phytochemistry*, 2007, 68, 150-175. Salts may include salts with anions such as chloride, bromide, iodide, nitrate, sulfate, bisulfate, sulfite, bisulfate, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluoromethansulfonate, ethanesulfonate, benzenesulfonate, p-toluenesulfonate, p-trifluoromethylbenzenesulfonate, hydroxide, aluminates and borates.

In some embodiments, the nanoparticles comprise a surfactant such as an anionic polymer, a phospholipid.

In some embodiments, the nanoparticles comprise an anionic polymer.

In some embodiments, the anionic polymer is an anionic polysaccharide.

In some embodiments, the anionic polymer is a sulfated polysaccharide.

In some embodiments, the anionic polymer is an anionic aminoglycan polymer.

In some embodiments, the anionic polymer is a sulfated aminoglycan polymer.

In some embodiments, the nanoparticles comprise berberine and the anionic polymer in a ratio in the range from about 1:5 to about 5:5, e.g., about 1:5; about 2:5; about 3:5; about 4:5 or about 5:5 by weight.

Examples of suitable anionic polymers include heparin, chondroitin sulfate, dermatan sulfate. keratan sulfate, fucoidan, and hyaluronic acid.

In some embodiments, the nanoparticles comprise heparin.

In some embodiments, the nanoparticles comprise berberine and heparin in a ratio in the range from about 1:5 to about 5:5, e.g., about 1:5; about 2:5; about 3:5; about 4:5 or about 5:5 by weight.

In some embodiments, the nanoparticles comprise a polysaccharide.

In some embodiments, the nanoparticles comprise a lipopolysaccharide.

In some embodiments, the nanoparticles comprise an aminoglycoside polymer.

In some embodiments, the nanoparticles comprise chitosan.

In some embodiments, the nanoparticles comprise berberine, heparin and chitosan.

In some embodiments, the nanoparticles comprise heparin and chitosan in a ratio of about 5:1 to 5:5 by weight, e.g., about 5:1 to about 5:2.5, e.g., about 5:1, about 5:1.5, about 5:2 or about 5:2.5.

In some embodiments, the nanoparticles comprise berberine, heparin and chitosan in a ratio of about 2:5:1.5, about 3:5:1.5 or about 4:5:1.5 by weight.

In some embodiments, the nanoparticles can be berberine nanoparticles using chitosan and fucoidan-taurine conjugate, e.g., as described in Wu et al., Delivery of Berberine Using Chitosan/Fucoidan-Taurine Conjugate Nanoparticles for Treatment of Defective Intestinal Epithelial Tight Junction Barrier, *Mar. Drugs,* 2014, 12, 5677-5697. In some embodiments, the nanoparticles can be berberine nanoparticles in nano-sized PLGA, e.g., as described by Khemani, et al., Encapsulation of Berberine in Nano-Sized PLGA Synthesized by Emulsification Method, ISRN *Nanotechnology,* 2012, Article ID 187354. In some embodiments, the nanoparticles can be nano-liposomes prepared using phospholipids, e.g., lipids prepared using lecithin, cholesterol and dihexadecyl phosphate. The liposomes can be coated, e.g., with chitosan. Nguyen et al., Chitosan-coated nano-liposomes for the oral delivery of berberine hydrochloride. *J. Mater. Chem. B,* 2014, 2, 7149-7159.

In some embodiments, the nanoparticles have a zeta ($\zeta$) potential in the range from about −10 to about −50 mV, e.g., about −10 mV, about −15 mV, about −20 mV, about −25 mV, about −30 mV, about −35 mV, about −40 mV, about −45 mV, or about −50 mV.

In some embodiments, the nanoparticles have a mean particle size in the range from about 5 nm to about 500 nm. In some embodiments, the nanoparticles have a mean particle size in the range from about 5 nm to about 200 nm. In some embodiments, the nanoparticles have a mean particle size in the range from about 10 nm to about 100 nm. In some embodiments, the nanoparticles have a mean particle size in the range from about 20 nm to about 100 nm.

In some embodiments, the nanoparticles have a mean particle size in the range from about 5 nm to about 1000 nm, e.g., about 10 nm to about 1000 nm, about 20 nm to about 1000 nm, about 50 nm to about 1000 nm, about 100 nm to about 1000 nm, about 200 nm to about 1000 nm; e.g., about 100 nm, about 200 nm, about 300 nm, about 400 nm, about 500 nm, about 600 nm, about 700 nm, about 800 nm, about 900 nm, or about 1000 nm.

The mean size of the nanoparticles described herein can be about 1 nm to about 1000 nm. In some embodiments, the size is in the range from about 5 nm to about 1000 nm, from about 5 nm to about 500 nm, from about 5 nm to about 400 nm, from about 5 nm to about 300 nm, from about 5 nm to about 200 nm, from about 5 nm to about 100 nm, from about 20 nm to about 200 nm, from about 40 nm to about 200 nm, from about 60 nm to about 200 nm, from about 20 nm to about 180 nm, from about 40 nm to about 180 nm, from about 60 nm to about 180 nm, from about 20 nm to about 160 nm, from about 40 nm to about 160 nm, from about 60 nm to about 160 nm, and/or from about 75 nm to about 150 nm.

In some embodiments, the nanoparticles present within a population, e.g., in a composition, can have substantially the same shape and/or size (i.e., they are "monodisperse"). For example, the particles can have a distribution such that no more than about 5% or about 10% of the nanoparticles have a diameter greater than about 10% greater than the average diameter of the particles, and in some cases, such that no more than about 8%, about 5%, about 3%, about 1%, about 0.3%, about 0.1%, about 0.03%, or about 0.01% have a diameter greater than about 10% greater than the average diameter of the nanoparticles.

In some embodiments, the diameter of no more than 25% of the nanoparticles varies from the mean nanoparticle diameter by more than 150%, 100%, 75%, 50%, 25%, 20%, 10%, or 5% of the mean nanoparticle diameter. It is often desirable to produce a population of nanoparticles that is relatively uniform in terms of size, shape, and/or composition so that most of the nanoparticles have similar properties. For example, at least 80%, at least 90%, or at least 95% of the nanoparticles produced using the methods described herein can have a diameter or greatest dimension that falls within 5%, 10%, or 20% of the average diameter or greatest dimension. In some embodiments, a population of nanoparticles can be heterogeneous with respect to size, shape, and/or composition. In this regard, see, e.g., WO 2007/150030, which is incorporated herein by reference in its entirety.

In some embodiments, the nanoparticles are spherical or substantially spherical in shape.

In some embodiments, the nanoparticles comprise berberine, an analog or derivative thereof, or a salt of berberine, its analogs or derivatives along with an anionic polysaccharide such as heparin and a lipopolysaccharide such as chitosan. To increase the therapeutic efficacy of berberine without the side effects, some studies were devised to increase its bioavailability. One of these studies is the creation of loadable nanoparticles for drug transport. Heparin is a highly sulfated glycosaminoglycan useful as an anticoagulation medicine. Besides its anticoagulation effect, heparin has anti-inflammation and immunomodulation effect. Mousavi et al., Anti-Inflammatory Effects of Heparin and Its Derivatives: A Systematic Review. *Adv. Pharmacol. Sci.,* 2015, 2015, 507151. Several studies have proven anti-asthma effect of heparin. Avadi et al. Preparation and characterization of insulin nanoparticles using chitosan and Arabic gum with ionic gelation method. *Nanomedicine,* 2010, 6, 58-63. Heparin has negative icons which can interact with positive berberine to form nanoparticles. But these nanoparticles appear to have a heterogeneous size distribution with an oval donut shape. To make berberine-heparin nanoparticles more suitable, chitosan was incorporated to form berberine heparin chitosan hybridized nanoparticles which are spherical in shape with a relatively homogeneous size distribution. Avadi et al. Ex vivo evaluation of insulin nanoparticles using chitosan and arabic gum. *ISRN Pharm,* 2011; 2011, 860109. Chitosan, is created by treating crustacean shells with alkali sodium hydroxide, has shown to be useful in the delivery of combinational drugs, and has been proven to adhere to and open the tight junctions between epithelial cells, and thus can potentially increase the bioavailability of encapsulated drugs. Chen et al. Recent advances in chitosan-based nanoparticles for oral delivery of macromolecules. *Adv. Drug Deliv. Rev.,* 2013, 65, 865-79; Bowman et al. Differential biological and adjuvant activities of cholera toxin and *Escherichia coli* heat-labile enterotoxin hybrids. *Infect. Immun.,* 2001, 69, 1528-35.

In some embodiments, the nanoparticles can be prepared by conventional methods. Examples of methods for nanoparticle formulation include emulsification, e.g., by centrifugation, high speed mixing, or sonication, or by nano-precipitation techniques. For example, nanoparticles containing berberine, heparin and chitosan can be prepared by emulsification of an aqueous solution containing berberine, heparin and chitosan.

Additional Formulation Ingredients

In addition to the ingredients comprising the particles as described herein, the composition may also contain adjuvants such as preservatives, wetting agents, emulsifying agents, and dispersing agents. Prevention of the action of microorganisms may be ensured by the inclusion of various antibacterial and antifungal agents, e.g., paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

Compositions containing nanoparticles as described herein can be administered in various forms, depending on the disease or disorder to be treated and the age, condition, and body weight of the subject. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

A tablet may be made by compression or molding, optionally with one or more accessory ingredients. Compressed tablets may also be prepared using inert diluent, preservative, disintegrant (e.g., sodium starch glycolate or cross-linked sodium carboxymethyl cellulose), surface-active or dispersing agent. Molded tablets may be made by molding in a suitable machine a mixture of a powdered compound moistened with an inert liquid diluent.

Liquid dosage forms for oral administration include pharmaceutically acceptable emulsions, microemulsions, solutions, suspensions, syrups, and elixirs. In addition to the nanoparticles, the liquid dosage forms may contain inert diluents, such as, e.g., water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Suspensions, in addition to the nanoparticles, may contain suspending agents as, e.g., ethoxylated isostearyl alcohols, polyoxyethylene sorbitol and sorbitan esters, microcrystalline cellulose, aluminum metahydroxide, bentonite, agar-agar and tragacanth, and mixtures thereof.

The composition should be stable under the conditions of manufacture and storage and must be preserved against the contaminating action of microorganisms such as bacteria and fungi. Prolonged absorption of the injectable compositions can be brought about by including in the composition an agent that delays absorption, e.g., aluminum monostearate and gelatin.

Dosage and Administration

Actual dosage levels of the berberine in the compositions provided herein may be varied so as to obtain an amount of berberine, or analog or derivative of berberine, or the salt thereof, that is effective to achieve the desired therapeutic response for a particular subject, composition, and mode of administration, without being toxic to the subject. The content of the berberine should be in the range from 0.1 to 90 wt.-%, preferably 0.1 to 50 wt.-% of the composition as a whole, i.e. an amount which are sufficient to achieve the dosage range specified below.

Dosage forms or compositions containing berberine as described may contain, in general, a daily dosage of from 0.01 to 2000 mg of the compound is recommended for an adult human subject, and this may be administered in a single dose or in divided doses. The amount of berberine, or analog or derivative of berberine, or the salt thereof, which can be combined with a carrier material to produce a single dosage form will generally be that amount of berberine, or analog or derivative of berberine, or the salt thereof, that produces a therapeutic effect. In some embodiments, the nanoparticle compositions described herein can contain from about 0.01 mg to about 5000 mg of berberine, or an analog or derivative of berberine, or a salt thereof. One having ordinary skill in the art will appreciate that this embodies compositions containing about 0.01 mg to 0.1 mg, about 0.1 mg to about 1 mg, about 1 mg to about 5 mg, about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg, about 50 mg to about 100 mg, about 100 mg to about 200 mg, about 200 mg to about 300 mg, about 300 mg to about 400 mg, about 400 mg to about 500 mg, about 500 mg to about 1000 mg, about 1000 mg to about 2000 mg, about 2000 mg to about 3000 mg, about 3000 mg to about 4000 mg or about 4000 mg to about 5000 mg of berberine, or an analog or derivative of berberine, or the salt thereof.

The composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The precise time of administration and/or amount of the composition that will yield the most effective results in terms of efficacy of treatment in a given subject will depend upon the activity, pharmacokinetics, and bioavailability of a particular drug molecule, physiological condition of the subject (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The compositions can be included in a container, pack, or dispenser together with instructions for administration.

In some embodiments, the composition is administered orally. The composition can also be administered, e.g., parenterally, by injection or by inhalation.

In some embodiments, the composition is administered repeatedly.

In some embodiments, the composition is administered at a frequency of about four times per day.

In some embodiments, the composition is administered at a frequency of about three times per day.

In some embodiments, the composition is administered at a frequency of about two times per day.

In some embodiments, the composition is administered at a frequency of about once per day.

A particular advantage of using nanoparticles comprising berberine or analogs or derivatives of berberine, or salts of berberine, its analogs or derivative as described herein is the long-lasting therapeutic effects that are obtained by using the nanoparticle formulation. This may allow the methods of treatment to be carried out by administering the composition at frequencies of once per day or less.

In some embodiments, the composition is administered at a frequency of about every other day.

In some embodiments, the composition is administered at a frequency of about twice per week.

In some embodiments, the composition is administered at a frequency of about once per week.

In some embodiments, the composition is administered at a frequency of about once per two weeks.

In some embodiments, the composition is administered at a frequency of about twice per month.

In some embodiments, the composition is administered at a frequency of about once per month.

In some embodiments, the composition is administered at a frequency of about once per two months.

In some embodiments, the composition is administered at a frequency of about once per three months.

In some embodiments, the composition is administered at a frequency of about once per four months.

In some embodiments, the composition is administered at a frequency of about once per five months.

In some embodiments, the composition is administered at a frequency of about once per six months.

In some embodiments, the composition is administered at a frequency of about twice per year (semi-annually).

In some embodiments, the composition is administered at a frequency of about once per year (annually).

In some embodiments, the composition is administered at a frequency of about once per two years (biannually).

In some embodiments, a single administration is effective to treat the immunological disease for a period of at least about one week, at least about one month, at least about six months, at least about one year, or at least about two years.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Materials and Methods
Nanoparticle Preparation

Berberine Chloride, heparin (ranging from 17,000 kDa to 19,000 kDa) and chitosan (low molecular weight, 75-85% deacetylated) were purchased from Sigma Aldrich (St. Louis, Mo., USA), Acetic Acid (glacial) and NaOH (1 N) were purchased from Fisher Chemicals (Robinson Township, Pa., USA). All other chemicals and reagents were of analytical grade. Two compositions of nanoparticles (berberine/heparin/chitosan) were prepared by a simple ionic gelation method with magnetic stirring at room temperature. Table 1 lists the nanoparticle preparation conditions as well as the measured size distributions and zeta potential values for each test sample. First, berberine/heparin nanoparticles (Table 1) were prepared by combining aqueous berberine (2 mg ml-1) with aqueous heparin by flush mixing with a pipette tip at various weight ratios (berberine/heparin 2:5, 3:5, 4:5 by weight). Berberine/heparin/chitosan nanoparticles were then prepared at distinct weight ratios (berberine/heparin/chitosan 2:5:1, 3:5:1, 4:5:1, 2:5:1.5, 3:5:1.5, 4:5:1.5, 2:5:2, 3:5:2 and 4:5:2 by weight) by adding aqueous berberine/heparin solution (0.5 ml) to aqueous chitosan solution (0.5 ml, pH 6.0).

Characterization of Berberine Loaded Nanoparticles

The size distributions and zeta potential values of the prepared nanoparticles at DI water were measured using a dynamic light scattering analyzer (Zetasizer ZS90, Malvern Instruments, Malvern, UK). FTIR spectra of the prepared nanoparticles were recorded with a Fourier transform infrared spectrometer (Shimadzu Scientific Instruments, Columbia, Md.). TEM was employed to examine the morphology of the different composition of nanoparticles (berberine/heparin or berberine/heparin/chitosan nanoparticles). The nanoparticle suspension was placed on a 400 mesh copper grid coated with carbon. About 2 min after deposition the grid was tapped with a filter paper to remove surface water and negatively stained with phosphotungstic acid solution.

Determination of Drug Loading Efficiency of Berberine

To measure the berberine loading efficiency of the prepared nanoparticles the resulting solution containing berberine-loaded nanoparticles was centrifuged at 16,000 r.p.m. for 1 h at 4° C. The amount of free berberine in the supernatant was analyzed by high performance liquid chromatography (HPLC) with a UV detector (Jusco Co. 875-UV, Tokyo, Japan) and a reverse phase $C_{18}$ column and eluted with acetonitrile-0.04 M $H_3PO_4$ (42:58 vol. %) at a 1.0 mL min$^{-1}$ flow rate. The berberine loading efficiency (LE %) of nanoparticles was calculated using the equation: lE (%)= (total berberine−free berberine)/total berberine×100%

Murine Sensitization, Treatment and Challenge Protocols

Six-week-old female C3H/HeJ mice purchased from the Jackson Laboratory (Bar Harbor, Me.) were maintained in pathogen-free facilities at the Mount Sinai vivarium on peanut-free chow according to standard guidelines for the care and use of animals. Institute of Laboratory Animal Resources Commission of Life Sciences NRC. Guide for the Care and Use of Laboratory Animals: National Academic Press, 1996. As shown in FIG. 1, Mice were systemically sensitized with 0.5 mg Crude Peanut Extract (CPE) mixed with 2 mg Alum (Thermofisher, NJ) once a week for three weeks. Some mice were sensitized to egg white (EW) using a similar protocol. Subsequently, daily oral treatment with BBR-nanoparticles was administered in 4-week and 2-week phases with an interval of 2 weeks at times indicated. Mice were periodically challenged with systemic and oral challenges at approximately 6 week intervals, as indicated. In some experiments mice were given intraperitoneal injections of 100 μg of anti-CD8 or anti-IFNγ antibodies, one day prior and then twice weekly during treatment period.

Assessment of Hypersensitivity Reactions

Anaphylactic symptoms were observed over 30 minutes and grades 0-5 were used to score the reactions: 0—no signs; 1—scratching and rubbing around the snout and head, diarrhea without other systemic symptoms; 2—puffiness around the eyes and snout, redness around snout, pilar erecti, reduced activity, and/or decreased activity with increased respiratory rate; 3—Labored respiration, diarrhea accompanied by drop in body temperature, and labored respiration accompanied by drop in body temperature and sustained lack of voluntary motility, but activity after prodding, 4—Labored respiration, drop in body temperature, cyanosis around the mouth and the tail splaying of limbs with belly resting on cage floor, minimal or no activity after prodding, tremor and convulsions. 5—Death. Reactions with score 1 were defined as mild; scores 2 as moderate-to severe; score 3-4 as severe, score 5 very severe.

Measurement of Peanut and Egg White Specific Immunoglobulins

Microtitre plates were coated with defatted protein extracts of peanut or egg white (sample wells) and rat anti-mouse IgE (reference wells) and held overnight at 4° C. After washing three times, plates were blocked for 2 hours at room temperature with 2% BSA-PBS. After three washes plates were incubated with diluted serum samples overnight at 4° C. Biotinylated anti-IgE was added to the plates followed by avidin-peroxidase and ABTS substrate. An antigen capture method was used to detect WN-specific IgE. Briefly, microtitre plates were coated with anti-IgE antibodies and held overnight at 4° C. After 3 washes, plates were blocked as described above. Plates were then washed and diluted serum or mouse IgE was added and incubated at 4° C. overnight. After washing, biotinylated WN extract was added to sample wells and biotinylated anti-IgE was added to reference wells. Finally, all wells were developed by addition of avidin-HRP followed by ABTS substrate. Total IgA, peanut specific IgG1 and IgG2a levels were measured as described in a previous publication. Srivastava et al. Efficacy, safety and immunological actions of butanol-extracted Food Allergy Herbal Formula-2 on peanut anaphylaxis. *Clin. Exp. Allergy*, 2011, 41, 582-91; Lee et al., Oral administration of IL-12 suppresses anaphylactic reactions in a murine model of peanut hypersensitivity. *Clin. Immunol.*, 2001, 101, 220-8.

Splenocyte Culture and Cytokine Measurement

At termination of experiments mice were euthanized and single cell suspensions of splenocytes were cultured with 200 μg/mL CPE or medium alone for 72 hours under tissue culture conditions. Supernatants were harvested and stored at −80° C. till used. IL-4 and IFNγ were measured by commercial ELISA (BD Biosciences) according to the manufacturer's instructions.

Flow Cytometry

Cultured splenocytes were washed and processed for flow cytometric analysis. Cells were fluorescently stained for cell surface markers (CD3, CD8, CD4) in the presence of Fc-Block. After washing cells were fixed and permeablized and intracellular staining for IFNγ was performed. Data was acquired on an LSRII flow cytometer using FACSDiva and analyzed by FlowJo.

CpG Methylation Analysis

Genomic DNA from intestinal tissue preserved in All protect (Qiagen, MD) was isolated using an AllPrep mini DNA kit (Qiagen, MD). Isolated DNA was then bisulfite converted using an Epitect plus DNA Bisulfite kit (Qiagen, MD) as per manufacturer's instructions. Bisulfite converted DNA was used to amplify promoter region FoxP3 gene by PCR which were subsequently pyrosequenced using the Pyromark Q24 Pyrosequencing system and Pyromark software (Qiagen, MD) o determine methylation percentage of CpG residues at −71, −62, −53, −50, −35 relative to transcriptional start site. The following previously described PCR and sequencing primers were used. FoxP3 Fwd: 5'-TATATTTTTAGATGATTTGTAAAGGGTAAA (SEQ ID NO:1), FoxP3 Rev: 5'-Biotin-TCACCT-TAATAAAATAAACTACTA (SEQ ID NO:2), Sequencing primer: 5'-AAAAAATTGGATTATTAGAA (SEQ ID NO:3). Song et al., Maternal allergy increases susceptibility to offspring allergy in association with TH2-biased epigenetic alterations in a mouse model of peanut allergy. *J. Allergy Clin. Immunol.*, 2014, 134, 1339-45.e7; Liu et al., The ligase PIAS1 restricts natural regulatory T cell differentiation by epigenetic repression. *Science*, 2010, 330, 521-5; Liu et al., Combined inhaled diesel exhaust particles and allergen exposure alter methylation of T helper genes and IgE production in vivo. *Toxicol. Sci.*, 2008, 102, 76-81.

Statistical Analysis

Data were analyzed using GraphPad Prism. One Way ANOVA was applied to determine significant differences across treatment groups. Student's t test was used to analyze differences between selected groups. For data that were not normally distributed, the Mann-Whitney test was used with Dunn's post-test. Pearson correlation was used for regression analysis. P values less than P≤0.05 were considered significant.

Results

Example 1. Berberine/Heparin/Chitosan Nanoparticle Formulation Markedly Enhanced In Vivo BBR Uptake To address poor uptake and bioavailability of berberine, a nanoparticle delivery approach was developed. Berberine/heparin/chitosan nanoparticles were prepared by solubilizing berberine in an aqueous mixture of heparin/chitosan at a ratio of 2:4:1.5. (Table 1). Drug-loading of berberine in these nanoparticles approached 70% and physical characteristics of the particles were found to be within parameters ideal for gastrointestinal uptake. Serum berberine levels in mice given a single dose of berberine/heparin/chitosan nanoparticles were significantly increased compared to mice given berberine alone (FIG. 1).

Figure 2A:
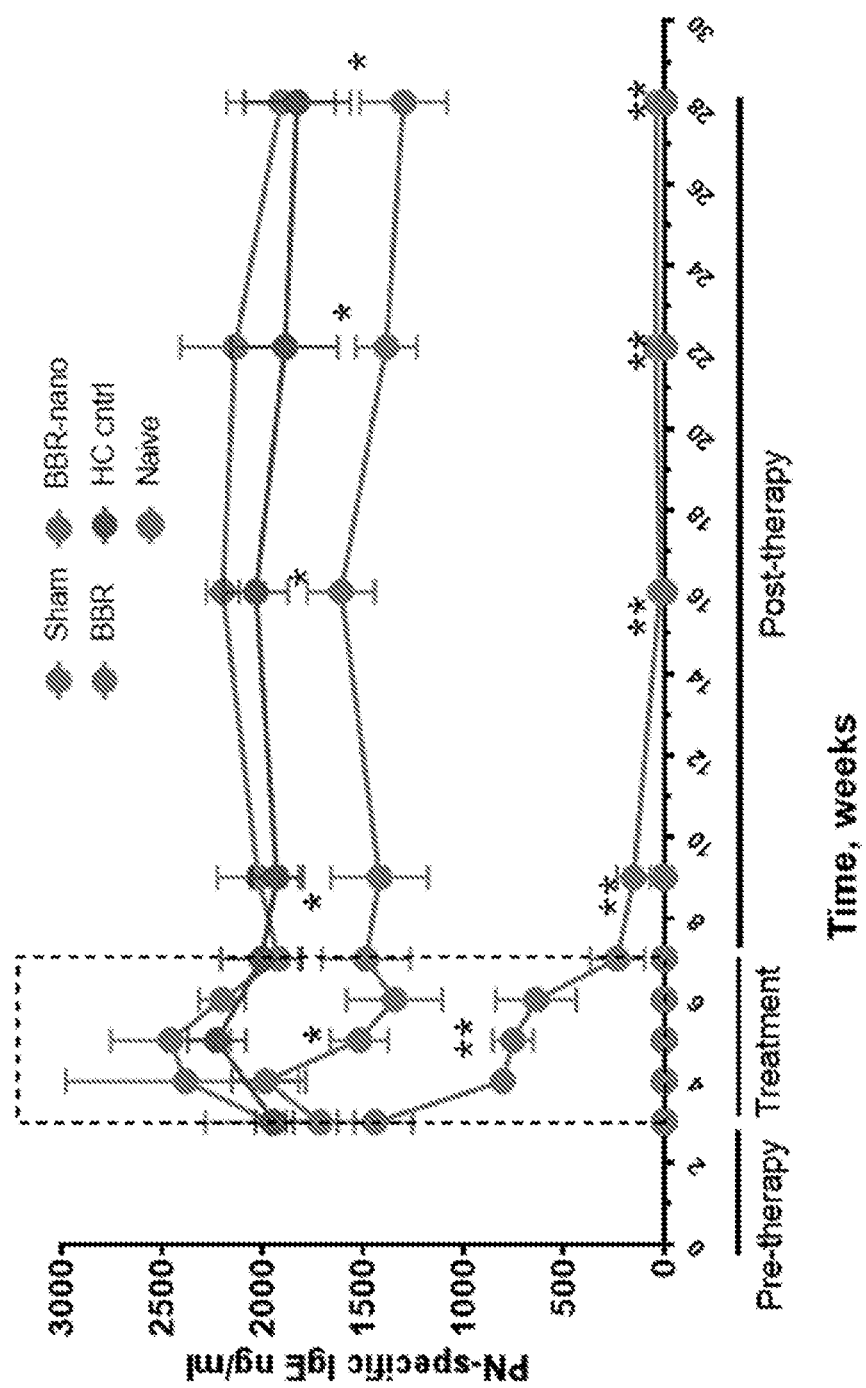
FIG. 2A is a plot showing peanut-specific IgE levels in serum from blood drawn from 10 mice at indicated times was measured by ELISA. Data shown as group Means±SEM. N=8-10 mice/group *$P<0.05$; **$P<0.01$ vs Sham.
Figure 2B:
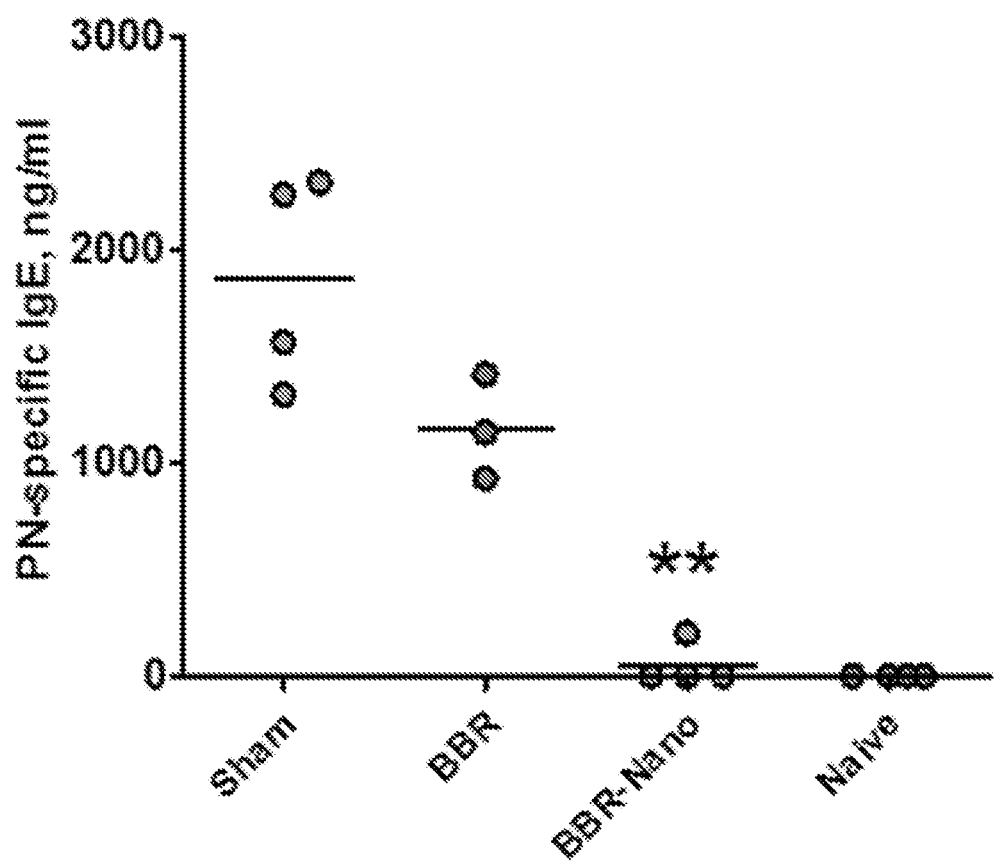
FIG. 2B is a plot showing peanut-specific IgE levels for mice were continued to be monitored at 20 weeks post-therapy were measured. Symbols in FIG. 2B indicate individual mice *$P<0.05$; **$P<0.01$ vs Sham.
Figure 2C:
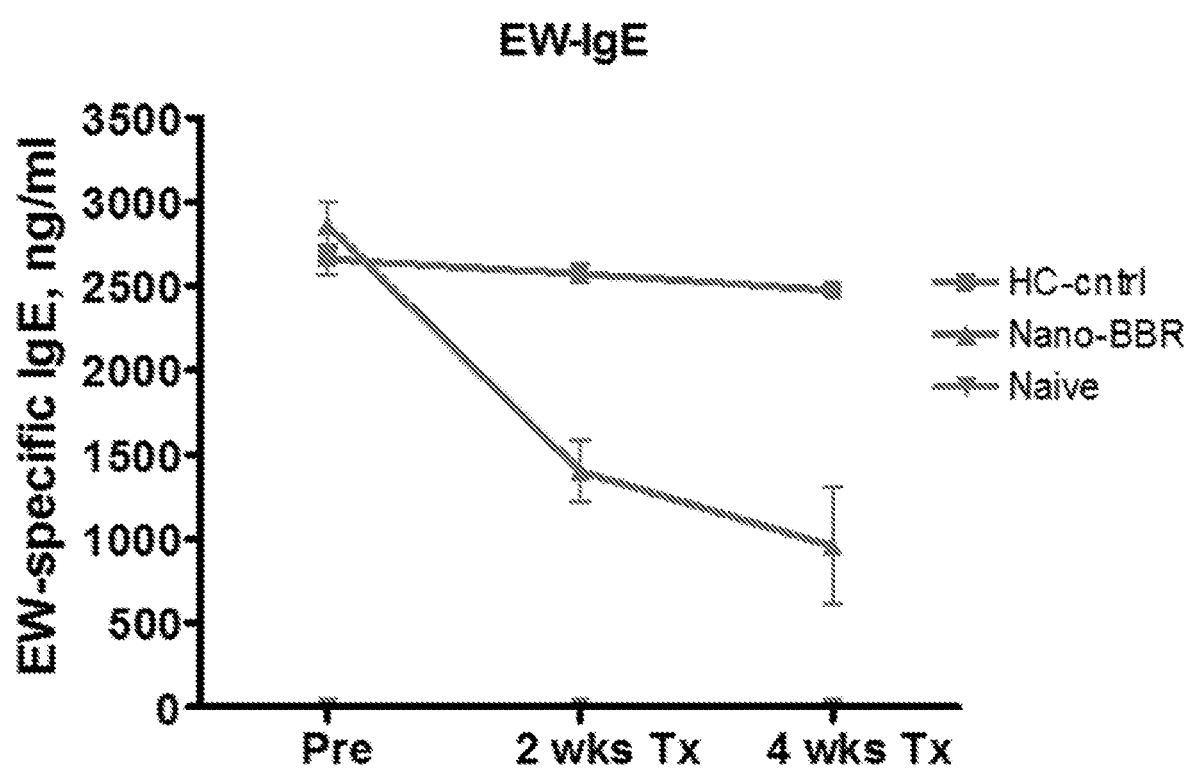
FIG. 2C is a plot showing egg-white specific IgE in serum measured by ELISA. Data shown as group Means±SEM. N=2-3 mice/group.

Example 2. Treatment of Peanut-Allergic Mice with Berberine/Heparin/Chitosan Nanoparticles Drastically and Persistently Reduced Peanut-Specific IgE Levels Systemically peanut sensitized mice received 2 course of oral berberine/heparin/chitosan nanoparticle therapy and IgE levels were measured periodically. Berberine/heparin/chitosan nanoparticle treatment reduced peanut-specific IgE to negligible or near negligible levels that continued to decline up to 9 weeks post-therapy and approached zero (FIG. 2A). This effect was extended up to 20 weeks post therapy (FIG. 2B). We also found that IgE reduction by berberine/heparin/chitosan nanoparticle therapy was not specific for peanut allergy. Berberine/heparin/chitosan nanoparticle treatment of egg white allergic mice resulted in significant reduction of IgE (FIG. 2C). Together these results suggest that use of berberine/heparin/chitosan nanoparticles is an efficacious IgE-reducing treatment applicable for multiple allergens.

Figure 3A:
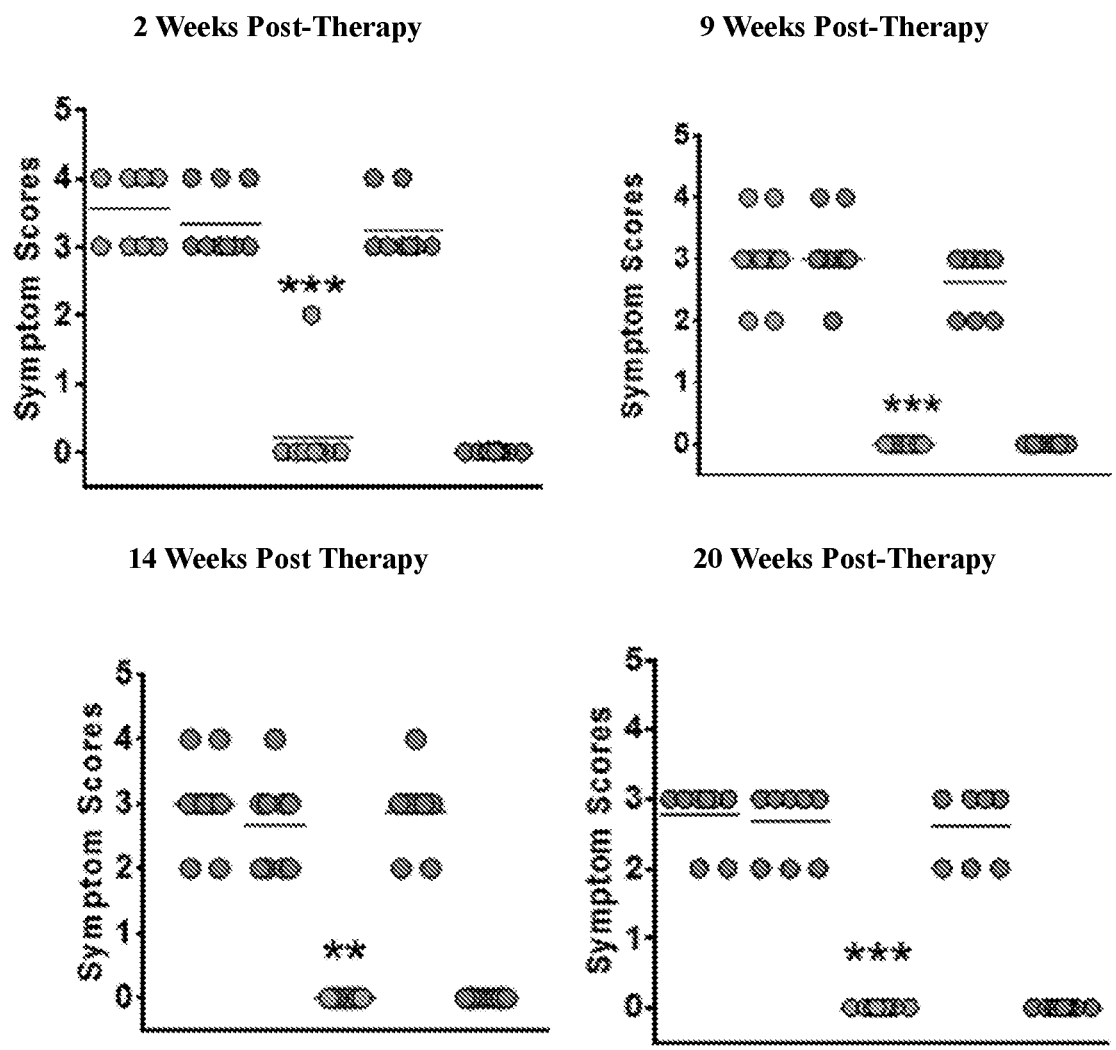
FIGS. 3A-C are plots showing the results of anaphylactic reactions to systemic or oral peanut challenge.
Figure 3B:
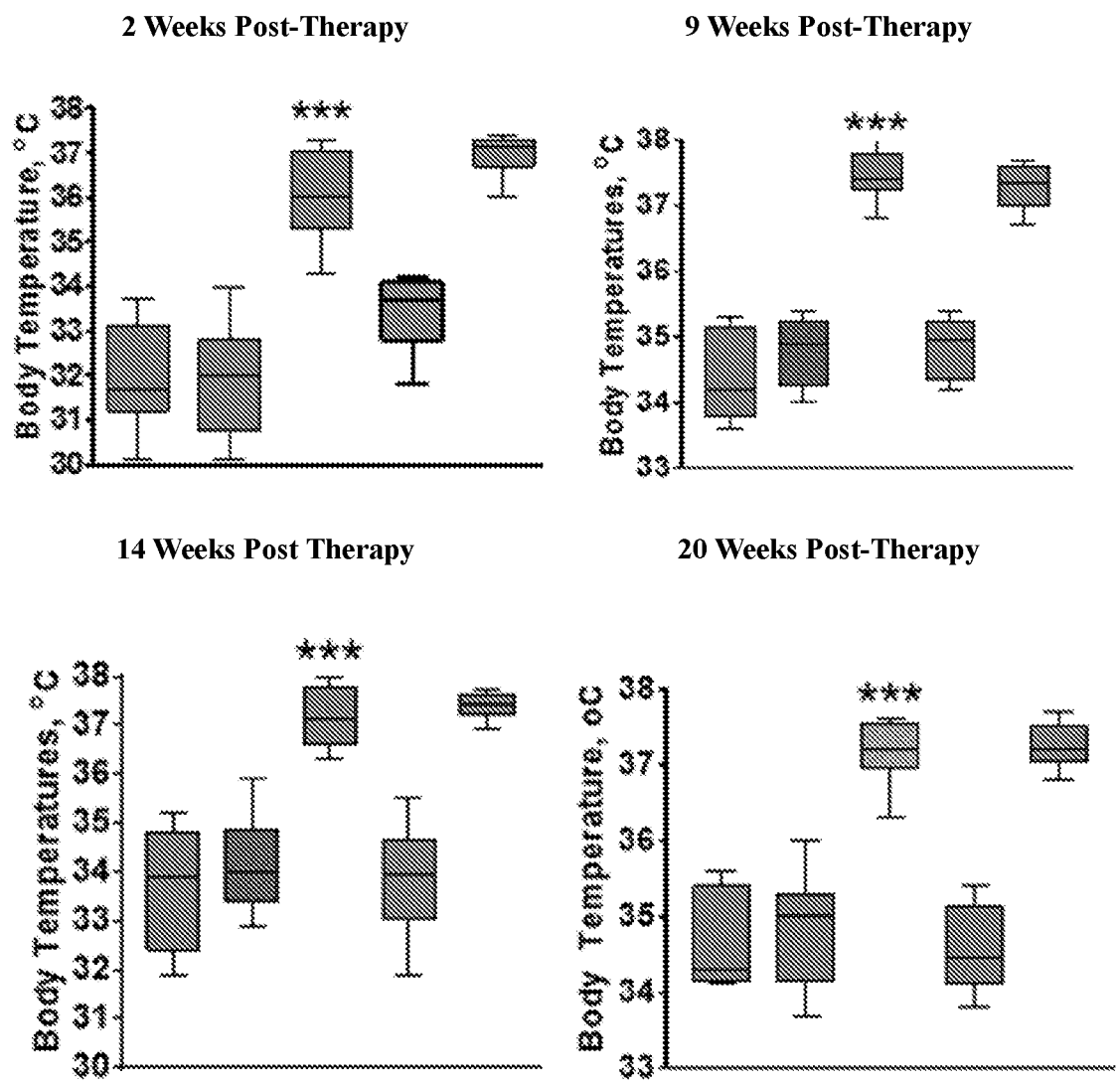
Figure 3C:
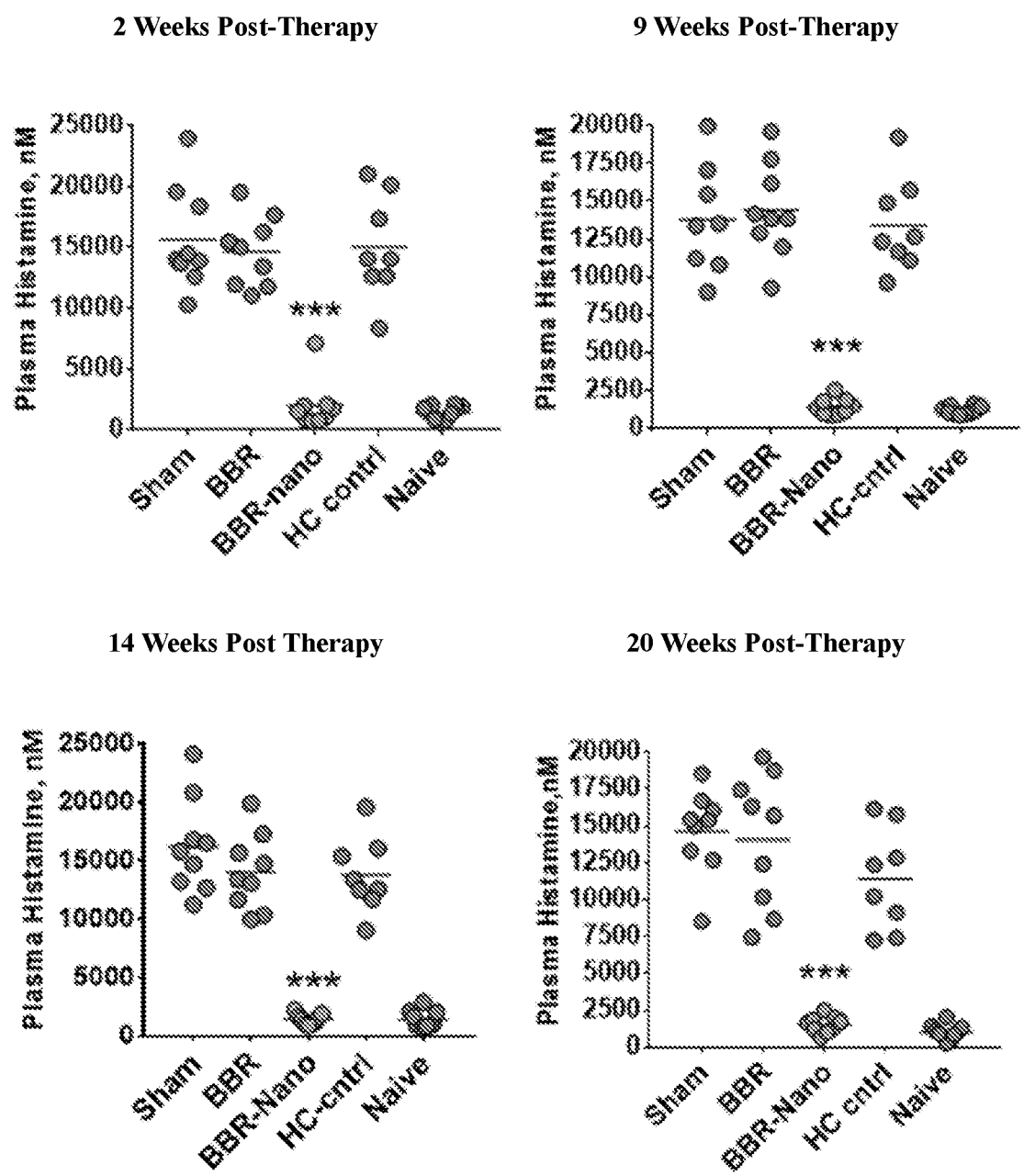

Example 3. Berberine/Heparin/Chitosan Nanoparticles Provided Protection Against Systemic and Oral Peanut Challenge Induced Anaphylaxis Mice systemically sensitized to peanut were treated with berberine/heparin/chitosan nanoparticles and systemically challenged at 2 and 14 weeks post-therapy and orally challenged at 9 and 20 weeks post-therapy (FIG. 3-C). Symptom scores (FIG. 3A), body temperature (FIG. 3B) and plasma histamine (FIG. 3C) were evaluated at each challenge. Mice in Berberine/heparin/chitosan nanoparticle treated groups were significantly protected following oral peanut challenge and showed only one mouse with visual signs of anaphylaxis or associated hypothermia at 2 weeks-post therapy. No signs of anaphylaxis were observed in this group at subsequent challenges (P<0.01-0.001 vs. Sham). Consistently, berberine/heparin/chitosan nanoparticle treated mice were significantly protected from anaphylaxis-associated hypothermia (P<0.001 vs. Sham) and plasma histamine levels in this group was significantly lower than Sham mice at all challenges (P<0.001 vs. Sham).

Figure 4:
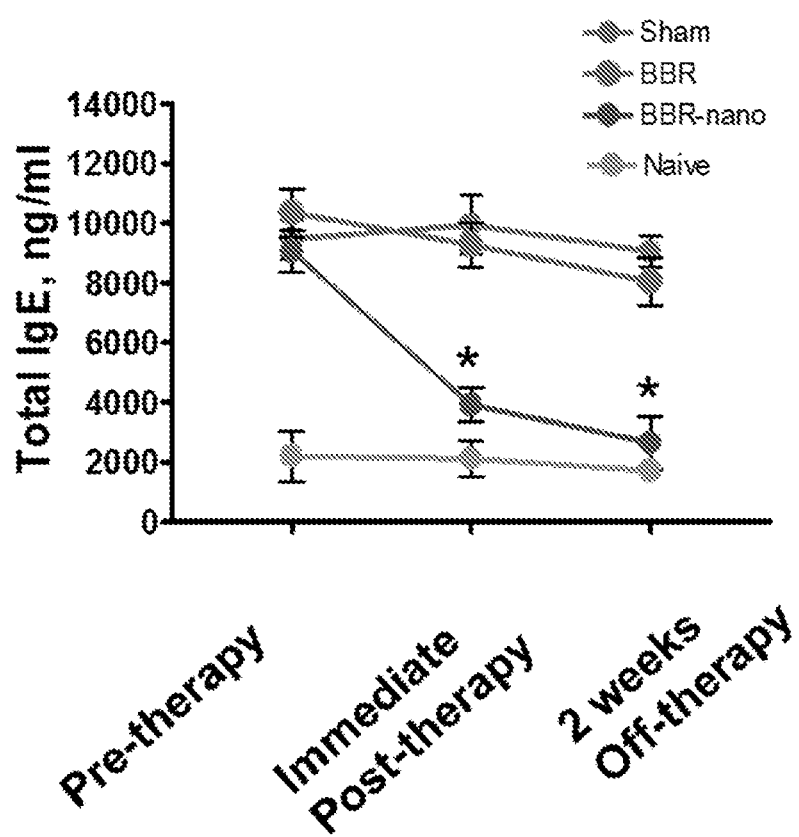
FIG. 4 is a plot of pre and post-therapy levels of total IgE measured by ELISA. Bars represent group Mean±SEM. N=8-10 mice per group.
Figure 5:
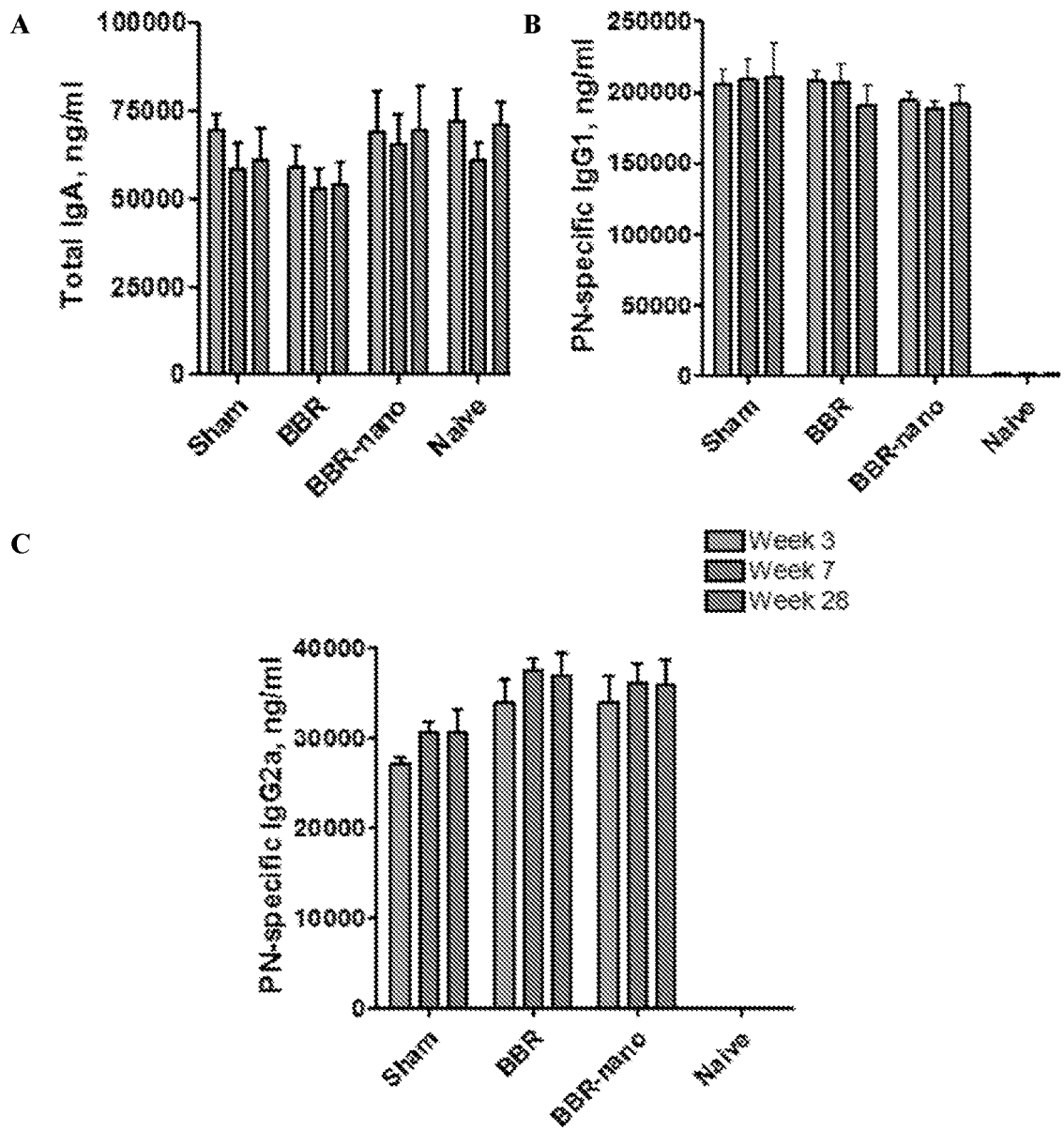
FIG. 5 is a plot of pre and post-therapy levels of A-total IgA, B-peanut-specific IgG1 and C-peanut-specific IgG2a measured by ELISA. Bars represent group Mean±SEM. N=8-10 mice per group.

Example 4. Berberine/Heparin/Chitosan Nanoparticle Therapies Reduced Total IgE Levels, but Did not Affect Total IgA or Specific IgG1/IgG2a Levels To determine if Berberine/heparin/chitosan nanoparticle therapy affected immunoglobulins other than specific-IgE, serum total IgE and IgA were evaluated. Berberine/heparin/chitosan nanoparticle treated peanut-allergic mice displayed decreases in total IgE (FIG. 4) but not total IgA (FIG. 5A). Further, no treatment effect was observed on peanut-specific IgG1/IgG2a levels (FIG. 5 B, C). These data show that berberine/heparin/chitosan nanoparticle therapy selectively targets IgE.

Figure 6:
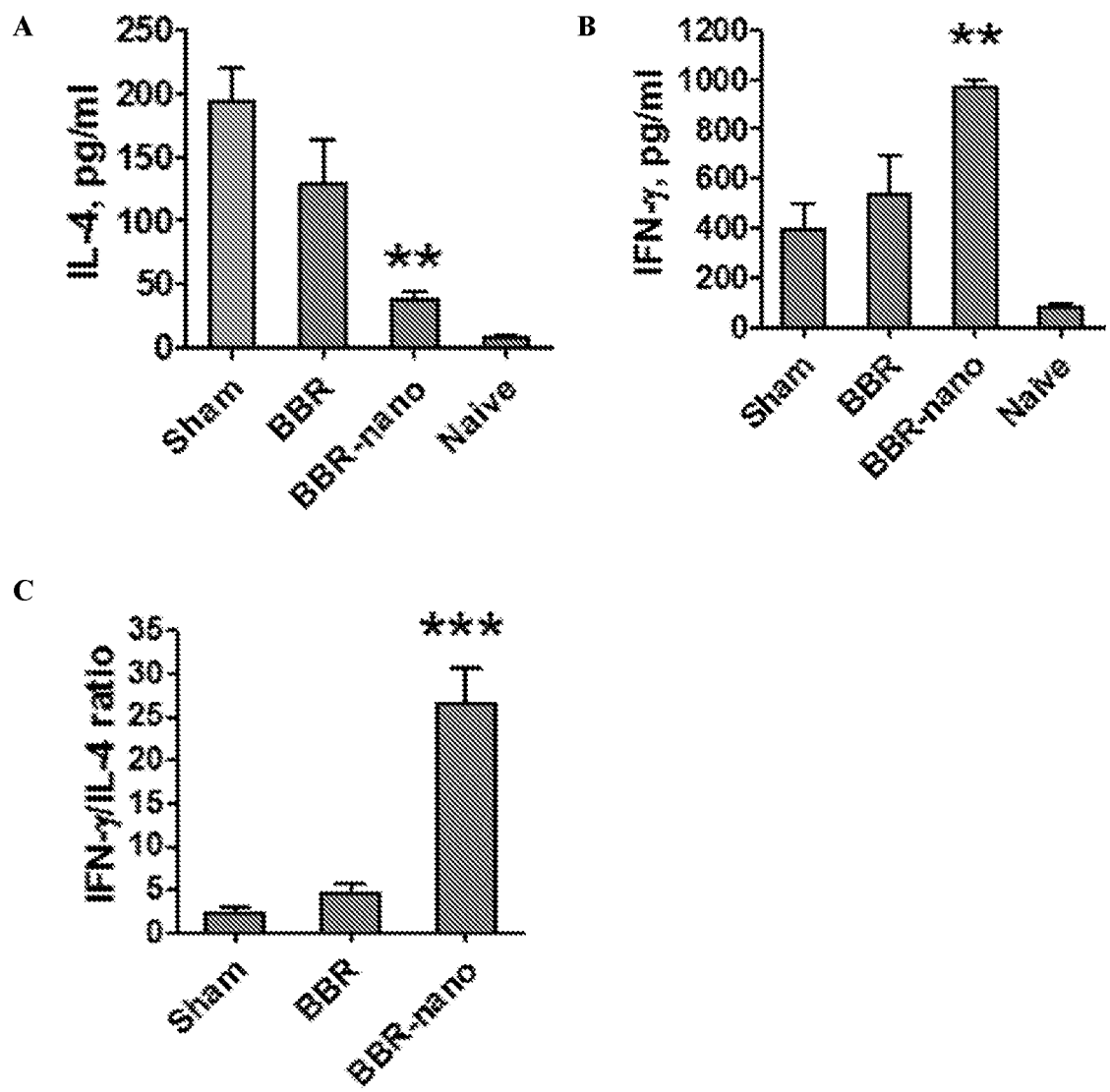
FIGS. 6A-C are plots showing cytokine levels in peanut-restimulated splenocyte cultures measured by ELISA.

Example 5. Berberine/Heparin/Chitosan Nanoparticle Treatment Confers Beneficial Cytokine Profile IL-4 is a critical Th2 cytokine that plays a major role in Igf production. The Th1 cytokine IFN-$\gamma$ is associated with outgrowth of allergy. We evaluated cytokines in peanut-restimulated splenocyte cultures. In mice treated with berberine/heparin/chitosan nanoparticles, IL-4 was significantly reduced (FIG. 6A, P<0.01 vs Sham) whereas a significant increase was observed for IFN-$\gamma$ (FIG. 6B, P<0.01 vs. Sham). Ratio of IFN-$\gamma$/IL-4 was also significantly increased in the berberine/heparin/chitosan nanoparticle treated group (FIG. 6C, P<0.01 vs. Sham).

Figure 7A:
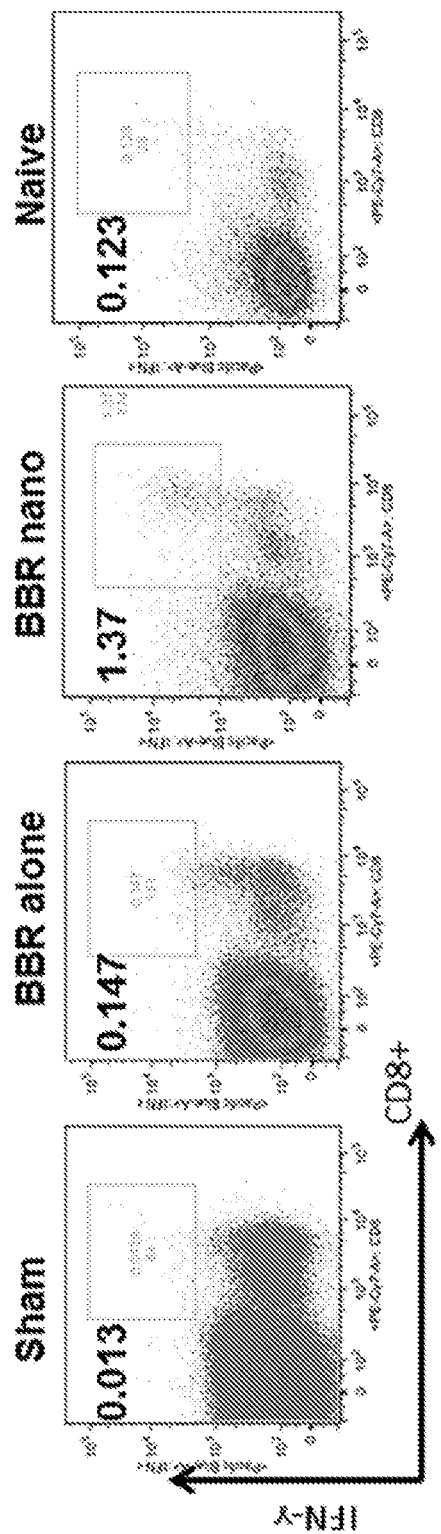
FIGS. 7A and B are plots of analysis of peanut-restimulated splenocytes showing that a population of CD8 T cells were increased in berberine/heparin/chitosan nanoparticle treated mice.
Figure 7B:
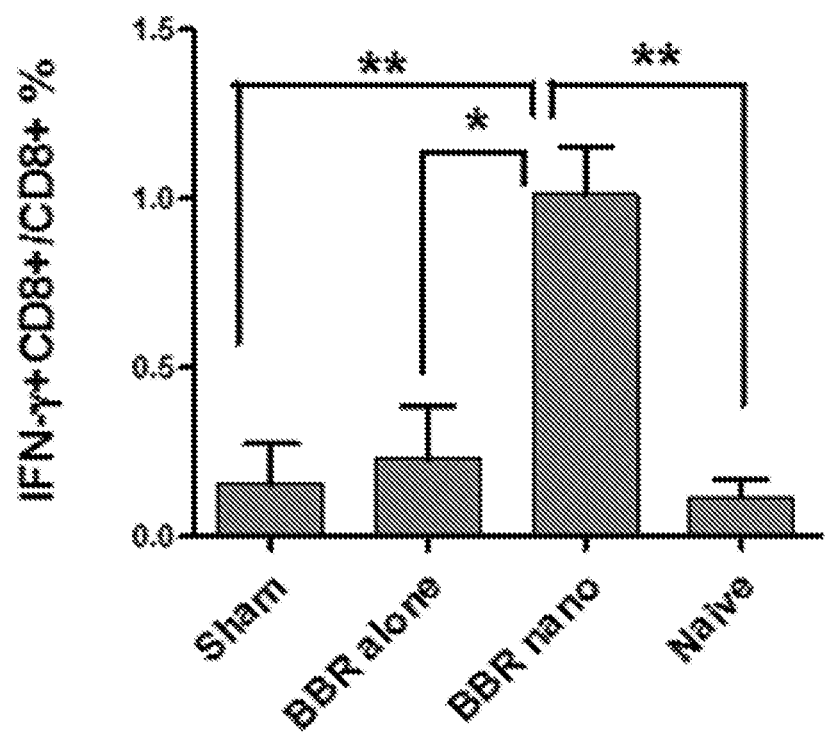
FIG. 7B is a plot of the numerical analysis of group data. Data shown as Means±SEM. *$P<0.05$; **$P<0.01$ vs. Sham.
Figure 8:
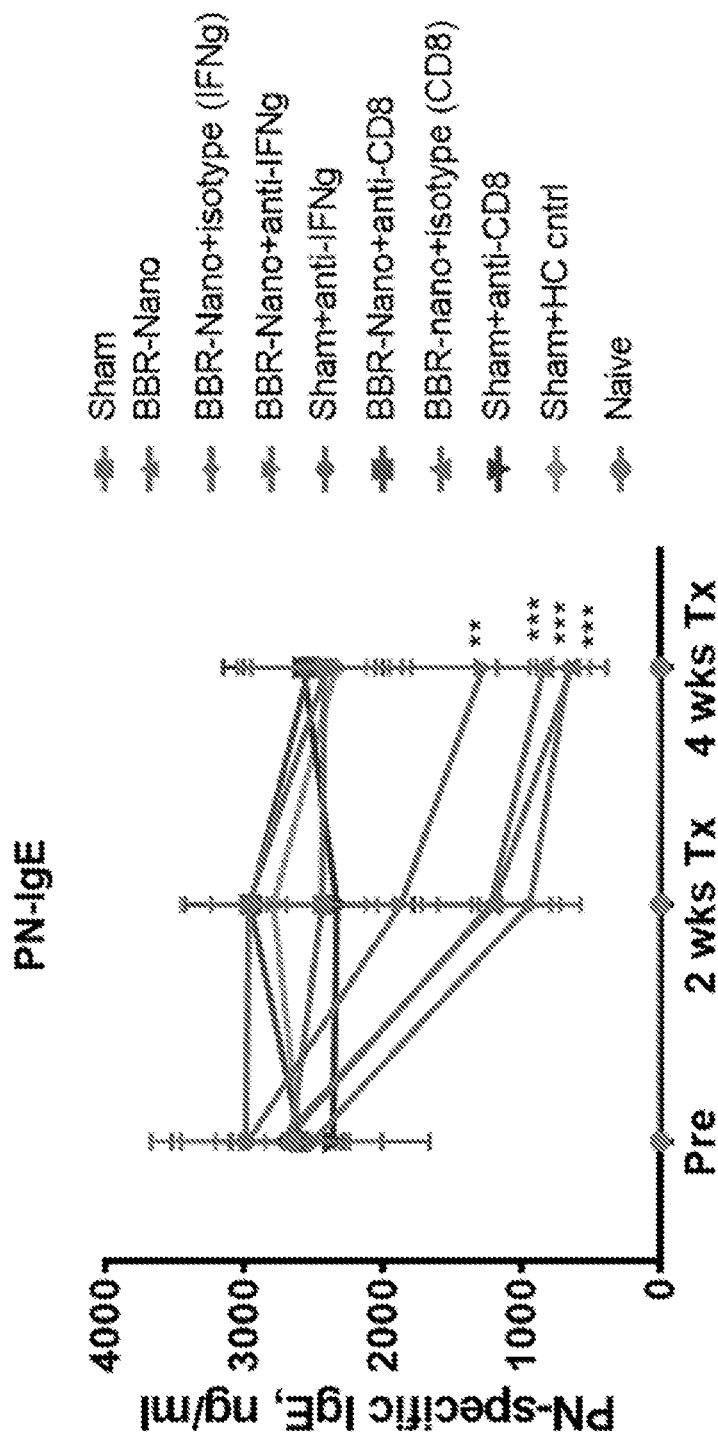
FIG. 8 is a plot of peanut-specific IgE levels in serum measured by ELISA in serum from blood drawn at indicated times was measured by ELISA. Data shown as group Means±SEM. N=3-5 mice/group *8$P<0.01$; ***$P<0.001$ vs Sham.

Example 6. CD8 T Cells are the Major Source of Elevated IFN-$\gamma$ in Berberine/Heparin/Chitosan Nanoparticle Treated Mice and are Functionally Important for Berberine/Heparin/Chitosan Nanoparticle Induced Reduction of IgE Having observed increased IFN-$\gamma$ in peanut-restimulated splenocyte cultures from in vivo treated mice, the cellular source was investigated. Analysis of intracellular cytokine staining for IFN-$\gamma$ in peanut-restimulated splenocytes showed that a population of CD8 T cells were increased in berberine/heparin/chitosan nanoparticle treated mice (FIGS. 7A and 7B; P<0.01 vs. Sham; P<0.05 vs. berberine alone). The functional contribution of CD8T cells and IFN-$\gamma$ to berberine/heparin/chitosan nanoparticle therapeutic effects also was assessed. Using depleting antibodies given prior to and during treatment, it was found that berberine/heparin/chitosan nanoparticle reduction of IgE was markedly impaired in mice given CD8 T cell depleting antibodies and to a lesser extent with IFN-$\gamma$ depleting antibodies (FIG. 8). Isotype control antibodies were without effect.

Figure 9D:
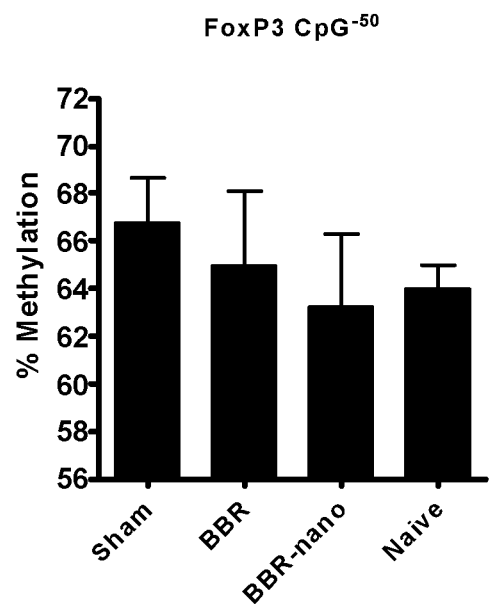
Figure 9E:
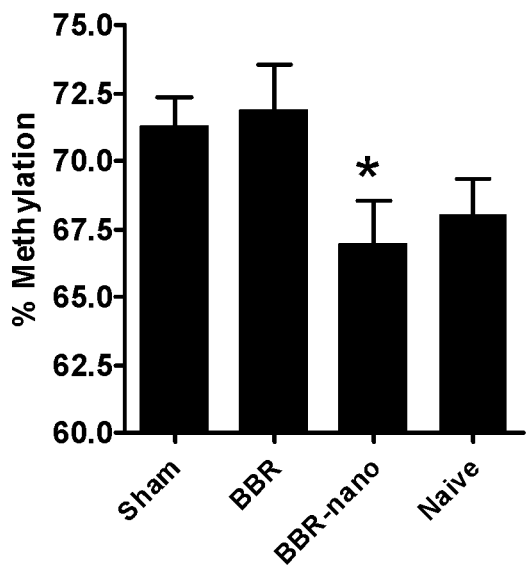
Figure 10:
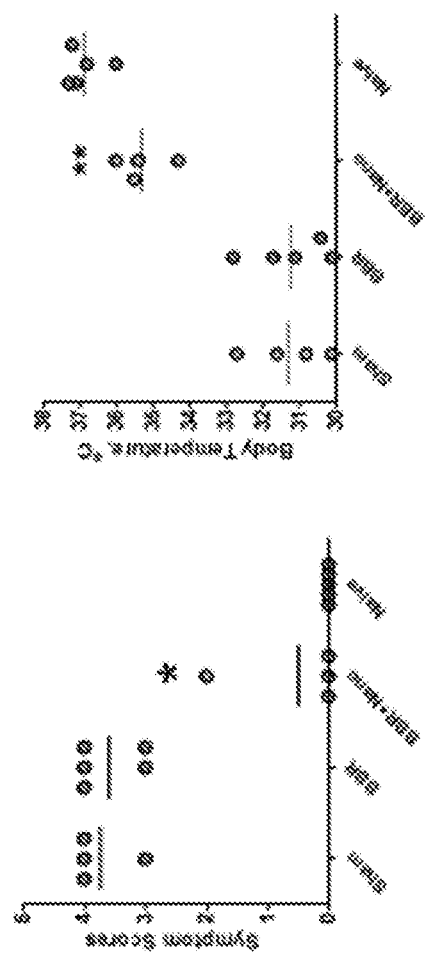
FIG. 10 is a pair of plots showing anaphylactic reactions to systemic peanut challenge. The left panel is a plot of symptom scores recorded 30 minutes after challenge. Symptom scores were assigned using the scoring key described herein; bars show group medians. The left panel is a plot of body temperature measured using a rectal probe immediately after assignment of the symptom score; bars show group means. N=3-5 mice/group *=$p<005$; ***=$p<0.001$.
Figure 11:
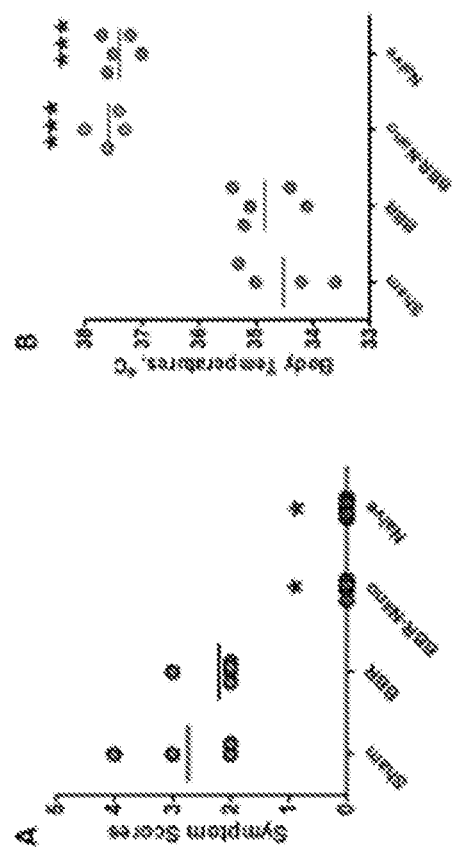
FIG. 11 is a pair of plots showing anaphylactic reactions to oral peanut challenge. The left panel is a plot of symptom scores recorded 30 minutes after challenge. Symptom scores were assigned using the scoring key described herein; bars show group medians. The left panel is a plot of body temperature measured using a rectal probe immediately after assignment of the symptom score; bars show group means. N=3-5 mice/group *=p<005; ***=p<0.001.

Example 7. Allergic Mice Treated with Berberine/Heparin/Chitosan Nanoparticles Show Demethylation of CpG Residues in the FoxP3 Promoter An enhanced Treg profile is associated with a beneficial and lasting outcome of anti-allergy therapy. To determine if berberine treatment of allergic mice establishes a positive Treg profile, methylation of CpG residues in the FoxP3 promoter was investigated using genomic DNA isolated from peripheral blood harvested 2 weeks after completing berberine/heparin/chitosan nanoparticle treatment. We found decreased in percent of methylation of several FoxP3 promoter CpG residues in samples from berberine/heparin/chitosan nanoparticle treated mice when compared to Sham mice or mice given berberine alone and trends for decreased methylation at other CpGs in the FoxP3 promoter (FIGS. 9A-D). When evaluated cumulatively, methylation levels in berberine/heparin/chitosan nanoparticle treated mice were significantly lower than in sham mice (FIG. 9E) suggesting therapy-induced elevation of FoxP3 expression and hence beneficial alteration of the regulatory T cell profile.

Discussion

Our current study reports a novel approach to IgE reduction using berberine delivered in heparin/chitosan nanoparticles. As less than 5% of berberine is taken up by the gastrointestinal tract, a strategy to increase GI retention of berberine is desirable. Berberine nanoparticles using mucoadhesive components such as chitosan and heparin have been described previously. Nanoparticles as drug carriers have been shown to enhance oral uptake of drugs, prolong their half-life and target drugs to lymphoid organs. Chitosan is a naturally occurring polysaccharide and is a safe, biocompatible and biodegradable mucoadhesive polymer. Heparin, though more known for its anti-coagulant properties, is also a polymeric polysaccharide that due to high negative charge is now being appreciated as a biopolymer ideal for drug carrier development. Additionally, heparin has been reported to possess anti-asthma effects and chitosan has been studied as an anti-allergy treatment. Using berberine delivery via heparin/chitosan nanoparticles it was demonstrated that berberine/heparin/chitosan nanoparticles dramatically inhibited IgE production in a murine peanut allergy model to the extent of complete reduction of peanut (PN)-specific IgE production in some mice. Virtual elimination of serum peanut-specific IgE has not been established by any previous intervention. That the reduction continues post-therapy is unique and impressive. Furthermore, it was found that IgE reduction by berberine/heparin/chitosan nanoparticle therapy is not restricted to peanut allergy as benefits were also observed in egg white allergic mice. These current data build upon previous published studies where it was demonstrated that berberine treatment of cultured U266 cells (an immortalized human IgE+ PC cell line) and human PBMCs caused significant reduction of IgE. Yang et al., Berberine and limonin suppress IgE production by human B cells and peripheral blood mononuclear cells from food-allergic patients. *Ann. Allergy Asthma. Immunol.*, 2014, 113, 556-64.e4. It was further found that berberine/heparin/chitosan nanoparticles also reduced total IgE levels similar to those in naïve mice, and importantly did not affect IgA and IgG levels. These data suggest that IgE production may be especially sensitive to regulation by berberine.

To provide mechanistic understanding of berberine/heparin/chitosan nanoparticle therapy reduction of IgE, the functional contribution of IFN$\gamma$-producing CD8 T cells which were chiefly responsible for elevated IFN-$\gamma$ in berberine/heparin/chitosan nanoparticle treated mice was investigated. Using antibody depletion, it was found that depleting CD8 T cells reversed berberine/heparin/chitosan nanoparticle IgE reduction whereas antibodies to IFN-$\gamma$ had only a slight effect. Further studies are needed to clarify how CD8 T cells regulate IgE production.

Previous reports have proposed that persistent IgE levels in mice and humans may be maintained either by direct development of long-lived IgE+ PCs and/or by replenishment of the IgE+PC pool by sequential switching of IgG1+ B cells to IgE+ B cells which then proceed to become short lived IgE+plasma cells. He et al., Biology of IgE production: IgE cell differentiation and the memory of IgE responses. *Curr. Top. Microbiol. Immunol.*, 2015, 388, 1-19; Erazo et al., Unique maturation program of the IgE response in vivo. *Immunity*, 2007, 26, 191-203; He et al., The distinctive germinal center phase of IgE+B lymphocytes limits their contribution to the classical memory response. *J. Exp. Med.*, 2013, 210, 2755-71. Regardless of their path to development, IgE+ PCs display high output of IgE and are chiefly responsible for maintenance of IgE levels. Jackson et al., Factors regulating immunoglobulin production by normal and disease-associated plasma cells. Biomolecules, 2015, 5, 20-40; Wu et al., Targeting IgE production in mice and humans. *Curr. Opin. Immunol.*, 2014, 31, 8-15. Hence vivo therapy with berberine/heparin/chitosan nanoparticles likely negatively regulates IgE levels by reducing numbers and/or activity of IgE+ PCs by preventing generation or survival of committed IgE+ PCs. Alternatively, it is possible that berberine/heparin/chitosan nanoparticles function to block IgE synthesis in IgE+ PCs by inducing a state of anergy. Our data regarding IgE reduction by berberine in U266 cells suggests that berberine has direct effects on IgE-plasma cell function. We are actively investigating definitive signaling mechanisms underlying this effect. Interestingly, it was found that in vivo berberine/heparin/chitosan nanoparticle therapy resulted in hypomethylation of CpG residues of the murine FoxP3 promoter, indicating that berberine may promote enhanced Treg responses. Tregs have been recently shown to negatively regulate PC numbers via direct contact and influence susceptibility of PCs to FcγRIIb/immune-complex mediated death. Jang et al. Foxp3+ regulatory T cells control humoral autoimmunity by suppressing the development of long-lived plasma cells. *J. Immunol.*, 2011, 186, 1546-53. Importantly it appears that IgE+ PCs are more sensitive to Treg suppression as demonstrated in a study where it was shown that human B cell/Treg co-cultures resulted in reduced IgE but elevated IgG4 levels. Meiler et al. Distinct regulation of IgE, IgG4 and IgA by T regulatory cells and toll-like receptors. *Allergy*, 2008, 63, 1455-63. Thus, berberine/heparin/chitosan nanoparticle therapy may have direct and indirect mechanisms of action on IgE-producing plasma cells requiring further investigation.

In conclusion, we, for the first time, produced drastic and sustained reduction of IgE responses and protection of peanut anaphylaxis following both systemic and oral challenges. It also reduced total IgE to normal ranges. Importantly, IgA and IgG levels are not affected. It also induced demethylation of Foxp3 gene promoter, indicating a favorable epigenetic modification in this model. The berberine/heparin/chitosan nanoparticle therapeutic strategy may have the potential to substantially alter the landscape of allergy treatment.

TABLE 1

Physical characteristics of various compositions of Berberine:Heparin:Chitosan nanoparticles. Optimal ratio for nanoparticle formation and associated characteristics are in red.

| | Test of BBR:Hep ratio (BBR:Hep) | | | | Test of Chitosan doses with BBR:Hep ratio at 2:5 (BBR:Hep:Chito) | | | | Test of BBR doses at Hep:Chito ratio at 1.5:5 (BBR:Hep:Chito) | | |
|---|---|---|---|---|---|---|---|---|---|---|---|
| Ratios | 2:5 | 3:5 | 4:5 | 5:5 | 2:5:1 | 2:5:1.5 | 2:5:2 | 2:5:3 | 2:5:1.5 | 3:5:1.5 | 4:5:1.5 |
| Mean particle size (nm) | 400.5 ± 4.3 | 519.8 ± 5.8 | 793 ± 11.9 | X | 345.3 ± 4.6 | 326.7 ± 2.2 | 381.5 ± 9.2 | X | 326.7 ± 2.2 | 519.8 ± 5.8 | 793 ± 11.9 |
| Zeta potential (mV) | −33.74 ± 2.66 | −35.16 ± 1.4 | −40.53 ± 2.17 | X | −24.05 ± 2.94 | −19.79 ± 1.58 | −36.94 ± 3.0 | X | −19.79 ± 1.58 | −26.47 ± 1.46 | −36.11 ± 1.5 |
| Poly-dispersity | 0.300 ± 0.002 | 0.284 ± 0.003 | 0.330 ± 0.006 | X | ND | ND | ND | ND | ND | ND | ND |
| Drug loading (%) | ND | ND | ND | ND | ND | ND | ND | ND | 64.7 | 67.9 | 71.6 |

X-Aggregate formation observed.
ND: Not done.

REFERENCES

1. Hendeles L, Sorkness C A. Anti-immunoglobulin E therapy with omalizumab for asthma. Ann Pharmacother 2007; 41:1397-410.
2. Luger E O, Wegmann M, Achatz G, Worm M, Renz H, Radbruch A. Allergy for a lifetime? Allergol Int 2010; 59:1-8.
3. Gauvreau G M, Harris J M, Boulet L P, Scheerens H, Fitzgerald J M, Putnam W S, et al. Targeting membrane-expressed IgE B cell receptor with an antibody to the M1 prime epitope reduces IgE production. Sci Transl Med 2014; 6:243ra85.
4. Harris J M, Cabanski C R, Scheerens H, Samineni D, Bradley M S, Cochran C, et al. A randomized trial of quilizumab in adults with refractory chronic spontaneous urticaria. J Allergy Clin Immunol 2016.
5. Harris J M, Maciuca R, Bradley M S, Cabanski C R, Scheerens H, Lim J, et al. A randomized trial of the efficacy and safety of quilizumab in adults with inadequately controlled allergic asthma. Respir Res 2016; 17:29.
6. Srivastava K D, Kattan J D, Zou Z M, Li J H, Zhang L, Wallenstein S, et al. The Chinese herbal medicine formula FAHF-2 completely blocks anaphylactic reactions in a murine model of peanut allergy. J Allergy Clin Immunol 2005; 115:171-8.
7. Srivastava K, Zhang T, Yang N, Sampson H, Li X M. Anti-Asthma Simplified Herbal Medicine Intervention-induced long-lasting tolerance to allergen exposure in an asthma model is interferon-gamma, but not transforming growth factor-beta dependent. Clin Exp Allergy 2010; 40:1678-88.
8. Yang N, Wang J, Liu C, Song Y, Zhang S, Zi J, et al. Berberine and limonin suppress IgE production by human B cells and peripheral blood mononuclear cells from food-allergic patients. Ann Allergy Asthma Immunol 2014; 113:556-64.e4.
9. Singh I P, Mahajan S. Berberine and its derivatives: a patent review (2009-2012). Expert Opin Ther Pat 2013; 23:215-31.
10. Godugu C, Patel A R, Doddapaneni R, Somagoni J, Singh M. Approaches to improve the oral bioavailability and effects of novel anticancer drugs berberine and betulinic acid. PLoS One 2014; 9:e89919.
11. Wei S C, Dong S, Xu L J, Zhang C Y. Intestinal absorption of berberine and 8-hydroxy dihydroberberine and their effects on sugar absorption in rat small intestine. J Huazhong Univ Sci Technolog Med Sci 2014; 34:186-9.
12. Zhang X, Qiu F, Jiang J, Gao C, Tan Y. Intestinal absorption mechanisms of berberine, palmatine, jateorhizine, and coptisine: involvement of P-glycoprotein. Xenobiotica 2011; 41:290-6.
13. Guo Y, Li F, Ma X, Cheng X, Zhou H, Klaassen C D. CYP2D plays a major role in berberine metabolism in liver of mice and humans. Xenobiotica 2011; 41:996-1005.
14. Gui S Y, Wu L, Peng D Y, Liu Q Y, Yin B P, Shen J Z. Preparation and evaluation of a microemulsion for oral delivery of berberine. Pharmazie 2008; 63:516-9.
15. Mousavi S, Moradi M, Khorshidahmad T, Motamedi M. Anti-Inflammatory Effects of Heparin and Its Derivatives: A Systematic Review. Adv Pharmacol Sci 2015; 2015:507151.
16. Avadi M R, Sadeghi A M, Mohammadpour N, Abedin S, Atyabi F, Dinarvand R, et al. Preparation and characterization of insulin nanoparticles using chitosan and Arabic gum with ionic gelation method. Nanomedicine 2010; 6:58-63.
17. Avadi M R, Sadeghi A M, Mohamadpour Dounighi N, Dinarvand R, Atyabi F, Rafiee-Tehrani M. Ex vivo evaluation of insulin nanoparticles using chitosan and arabic gum. ISRN Pharm 2011; 2011:860109.
18. Chen M C, Mi F L, Liao Z X, Hsiao C W, Sonaje K, Chung M F, et al. Recent advances in chitosan-based nanoparticles for oral delivery of macromolecules. Adv Drug Deliv Rev 2013; 65:865-79.
19. Bowman C C, Clements J D. Differential biological and adjuvant activities of cholera toxin and *Escherichia coli* heat-labile enterotoxin hybrids. Infect Immun 2001; 69:1528-35.
20. Institute of Laboratory Animal Resources Commission of Life Sciences NRC. Guide for the Care and Use of Laboratory Animals: National Academic Press, 1996.
21. Srivastava K, Yang N, Chen Y, Lopez-Exposito I, Song Y, Goldfarb J, et al. Efficacy, safety and immunological actions of butanol-extracted Food Allergy Herbal Formula-2 on peanut anaphylaxis. Clin Exp Allergy 2011; 41:582-91.
22. Lee S Y, Huang C K, Zhang T F, Schofield B H, Burks A W, Bannon G A, et al. Oral administration of IL-12 suppresses anaphylactic reactions in a murine model of peanut hypersensitivity. Clin Immunol 2001; 101:220-8.
23. Song Y, Liu C, Hui Y, Srivastava K, Zhou Z, Chen J, et al. Maternal allergy increases susceptibility to offspring allergy in association with TH2-biased epigenetic alterations in a mouse model of peanut allergy. J Allergy Clin Immunol 2014; 134:1339-45.e7.
24. Liu B, Tahk S, Yee K M, Fan G, Shuai K. The ligase PIAS1 restricts natural regulatory T cell differentiation by epigenetic repression. Science 2010; 330:521-5.
25. Liu J, Ballaney M, Al-alem U, Quan C, Jin X, Perera F, et al. Combined inhaled diesel exhaust particles and allergen exposure alter methylation of T helper genes and IgE production in vivo. Toxicol Sci 2008; 102:76-81.
26. He J S, Narayanan S, Subramaniam S, Ho W Q, Lafaille J J, Curotto de Lafaille M A. Biology of IgE production: IgE cell differentiation and the memory of IgE responses. Curr Top Microbiol Immunol 2015; 388:1-19.
27. Erazo A, Kutchukhidze N, Leung M, Christ A P, Urban J F, Jr., Curotto de Lafaille M A, et al. Unique maturation program of the IgE response in vivo. Immunity 2007; 26:191-203.
28. He J S, Meyer-Hermann M, Xiangying D, Zuan L Y, Jones L A, Ramakrishna L, et al. The distinctive germinal center phase of IgE+B lymphocytes limits their contribution to the classical memory response. J Exp Med 2013; 210:2755-71.
29. Jackson D A, Elsawa S F. Factors regulating immunoglobulin production by normal and disease-associated plasma cells. Biomolecules 2015; 5:20-40.
30. Wu L C, Scheerens H. Targeting IgE production in mice and humans. Curr Opin Immunol 2014; 31:8-15.
31. Jang E, Cho W S, Cho M L, Park H J, Oh H J, Kang S M, et al. Foxp3+ regulatory T cells control humoral autoimmunity by suppressing the development of long-lived plasma cells. J Immunol 2011; 186:1546-53.
32. Meiler F, Klunker S, Zimmermann M, Akdis C A, Akdis M. Distinct regulation of IgE, IgG4 and IgA by T regulatory cells and toll-like receptors. Allergy 2008; 63:1455-63.

A number of embodiments of the invention have been described. Nevertheless, it will be understood that various modifications may be made without departing from the spirit and scope of the invention. Accordingly, other embodiments are within the scope of the following claims. Each reference, including all patent, patent applications, and publications, cited in the present application is incorporated herein by reference in its entirety.

What is claimed is:

1. A method of treating a subject sensitized to an allergen and suffering from an IgE-mediated immunological disorder, comprising orally administering to a subject sensitized to an allergen, a therapeutically effective amount of a nanoparticle composition comprising berberine, or a salt thereof, heparin and chitosan, said nanoparticles having a mean particle size of between 200 nm to about 1000 nm, and a zeta ($\zeta$) potential of between −10 to −50 mV, whereby said subject is protected for a period of time after said administration against anaphylaxis induced by said allergen.

2. A method according to claim 1, wherein berberine or a salt thereof, is encapsulated in the nanoparticles.

3. A method according to claim 1, wherein the nanoparticles comprise heparin and chitosan in a ratio of about 5:1 to 5:5 by weight.

4. A method according to claim 1, wherein the composition is administered at a frequency of about once per day.

5. A method according to claim 1, wherein the allergen is a food allergen.

6. A method according to claim 5, wherein the allergen is derived from peanuts, tree nuts, soy products, milk products, egg products, fish products, crustacean products, gluten or wheat products.

7. A method according to claim 3, wherein the ratio is about 5:1 to about 5:2.5, about 5:1, about 5:1.5, about 5:2 or about 5:2.5.

8. A method according to claim 6, wherein the tree nuts are almond, brazil nuts, cashew nuts, macadamia nuts or walnuts.

9. A method according to claim 4, wherein the protection against anaphylaxis persists for at least one week after cessation of administration of said composition.

10. A method according to claim 4, wherein the protection against anaphylaxis persists for at least one month after cessation of administration of said composition.

\* \* \* \* \*